(12) United States Patent
Jaax et al.

(10) Patent No.: US 8,626,297 B2
(45) Date of Patent: Jan. 7, 2014

(54) APPARATUS AND METHODS FOR CHARGING AN IMPLANTED MEDICAL DEVICE POWER SOURCE

(75) Inventors: Kristen Jaax, Santa Clarita, CA (US); Rafael Carbunaru, Valley Village, CA (US); Mun Pook Lui, Northridge, CA (US); Todd K. Whitehurst, Valencia, CA (US); Andrew DiGiore, Santa Monica, CA (US); Brett Daniel Schleicher, Valencia, CA (US); Gregory Baldwin, Seattle, WA (US); Michael A. Moffitt, Valencia, CA (US); Jeffery Van Funderburk, Stevenson Ranch, CA (US); Jim Makous, Saugus, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 1062 days.

(21) Appl. No.: 12/233,810

(22) Filed: Sep. 19, 2008

(65) Prior Publication Data
US 2009/0082835 A1 Mar. 26, 2009

Related U.S. Application Data

(60) Provisional application No. 60/974,062, filed on Sep. 20, 2007.

(51) Int. Cl.
*A61N 1/378* (2006.01)
(52) U.S. Cl.
USPC .......................................................... 607/33
(58) Field of Classification Search
USPC .................................................... 607/33, 61
See application file for complete search history.

(56) References Cited

U.S. PATENT DOCUMENTS

| | | | |
|---|---|---|---|
| 6,735,474 B1 | 5/2004 | Loeb et al. | |
| 6,735,475 B1 | 5/2004 | Whitehurst et al. | |
| 7,925,357 B2* | 4/2011 | Phillips et al. | 607/61 |
| 2005/0004619 A1 | 1/2005 | Wahlstrand et al. | |
| 2005/0288743 A1* | 12/2005 | Ahn et al. | 607/61 |

FOREIGN PATENT DOCUMENTS

WO WO 2004/103465 A1 12/2004

* cited by examiner

*Primary Examiner* — Eric D. Bertram
(74) *Attorney, Agent, or Firm* — Vista IP Law Group LLP

(57) ABSTRACT

Apparatus and methods for charging an implanted medical device.

18 Claims, 25 Drawing Sheets

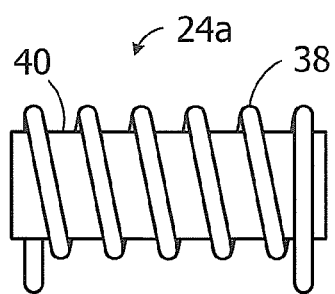 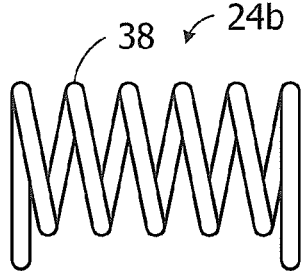 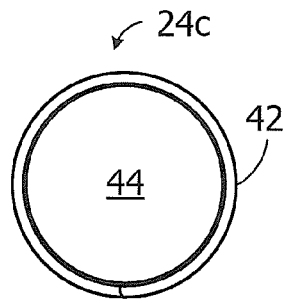
*FIG. 2A*     *FIG. 2B*     *FIG. 2C*
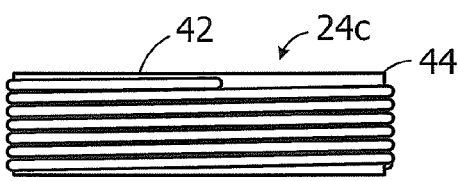
*FIG. 2D*
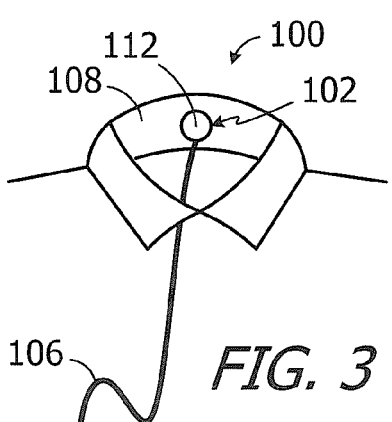 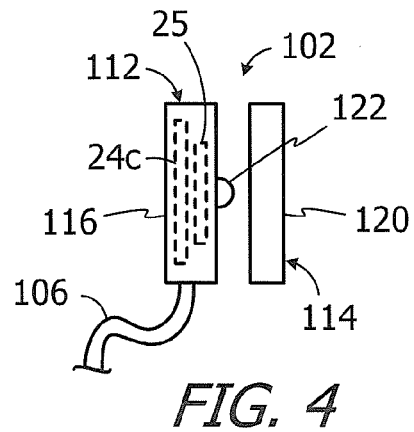
*FIG. 3*     *FIG. 4*
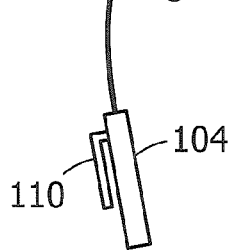 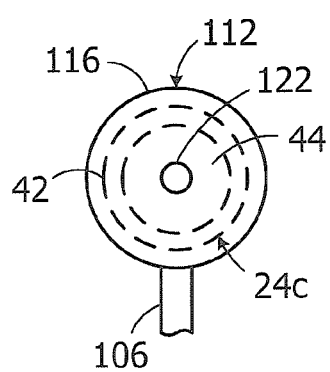 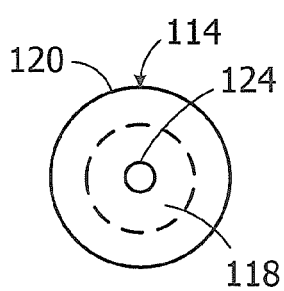
*FIG. 5*     *FIG. 6*

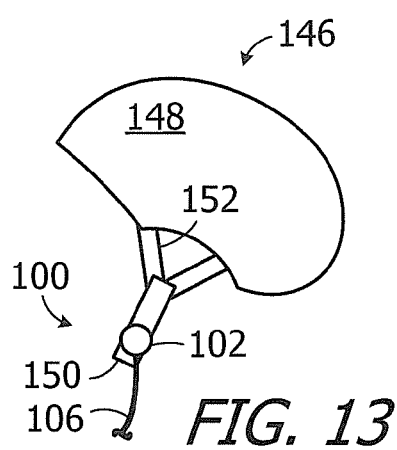
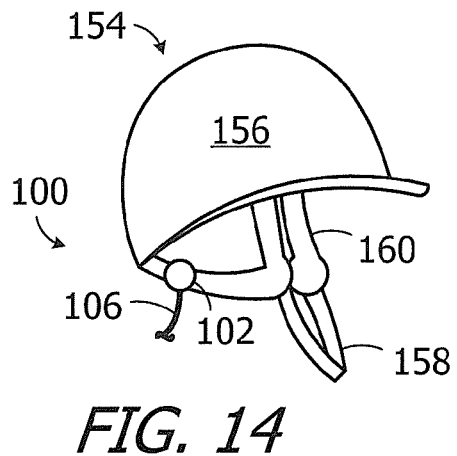
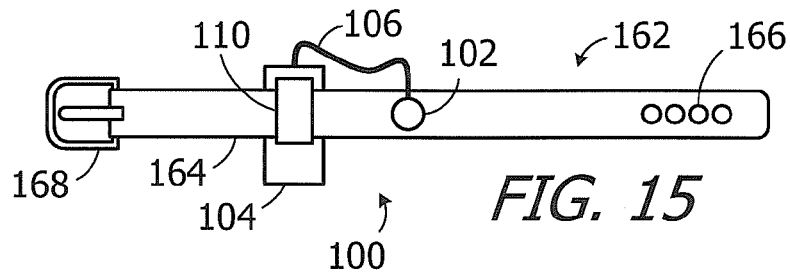
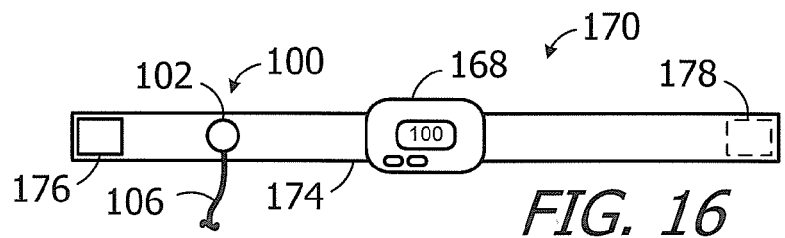
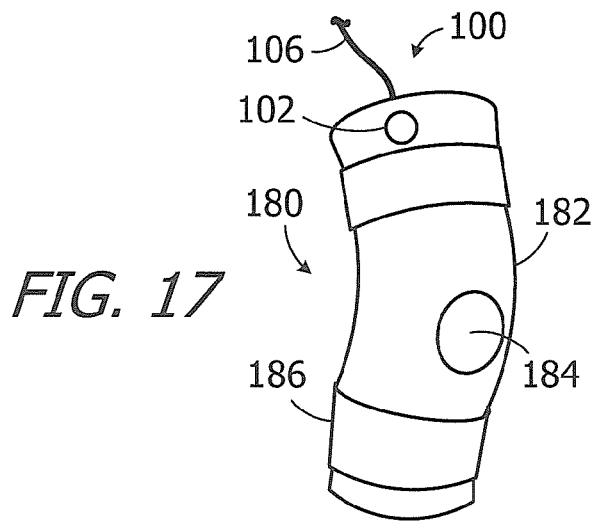

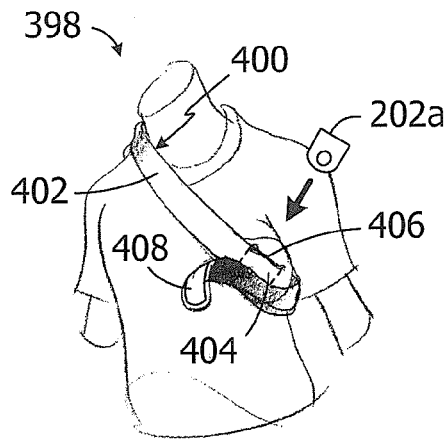
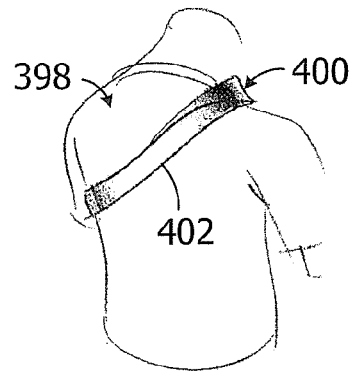
FIG. 42　　　　　FIG. 43
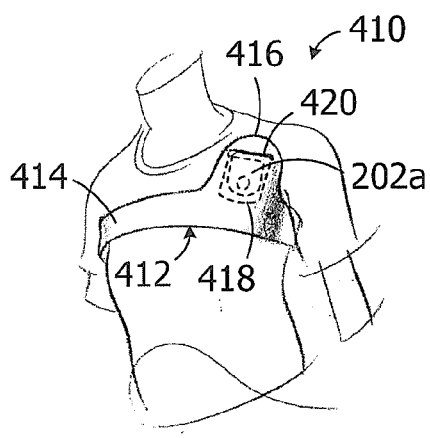
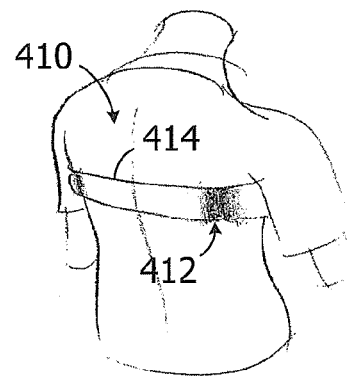
FIG. 44　　　　　FIG. 45
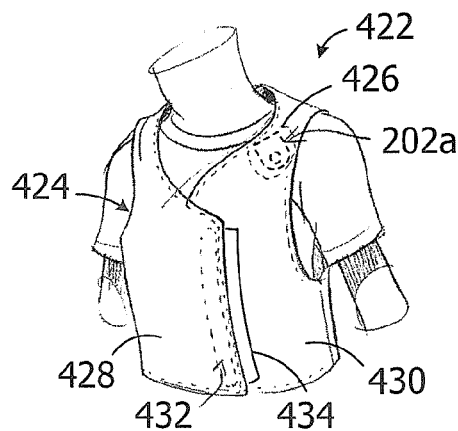
FIG. 46

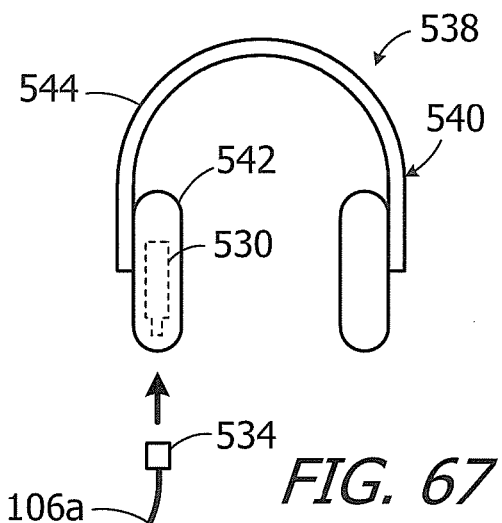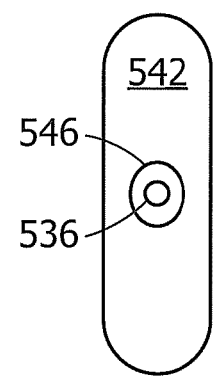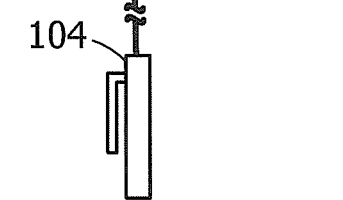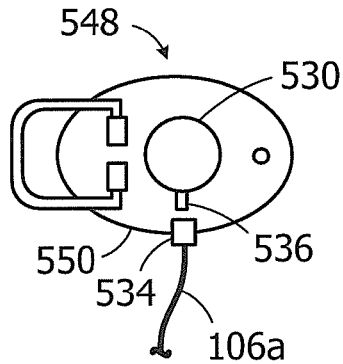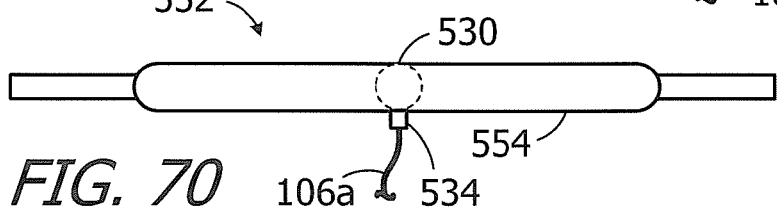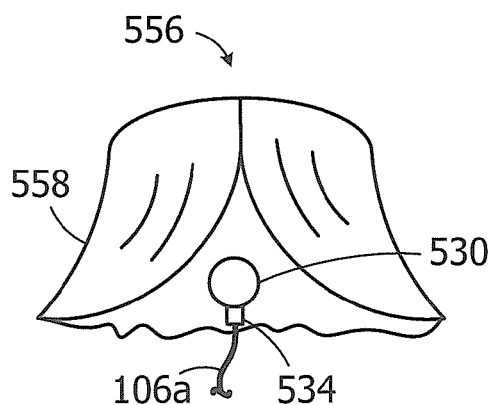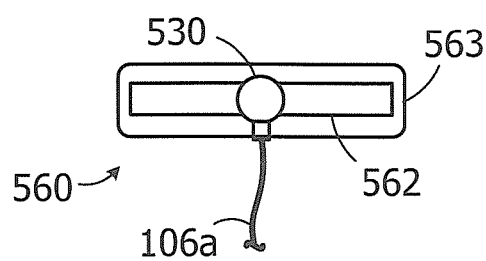

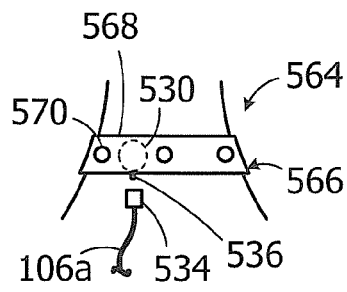
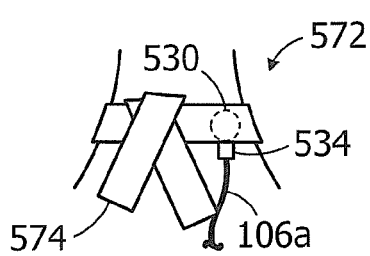
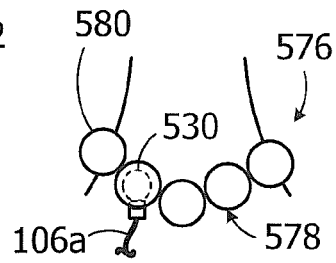
FIG. 73   FIG. 74   FIG. 75
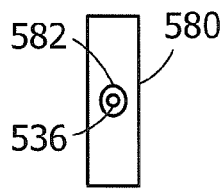
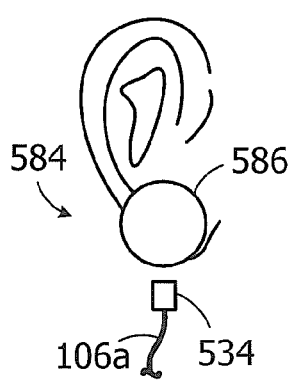
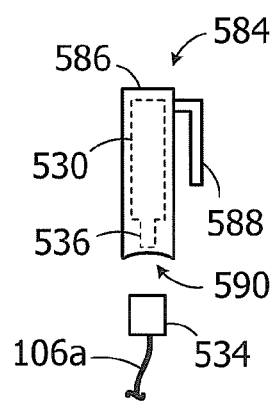
FIG. 76   FIG. 77   FIG. 78
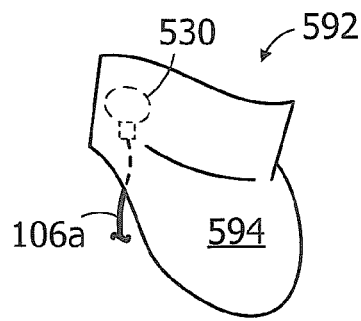
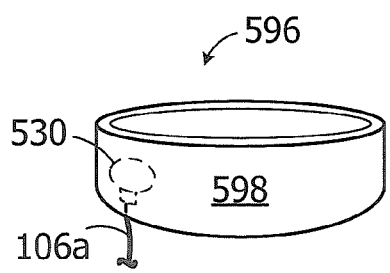
FIG. 79   FIG. 80

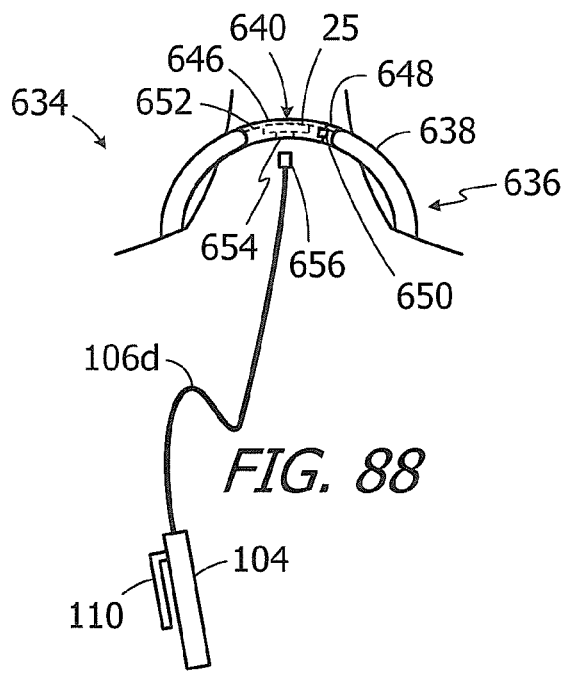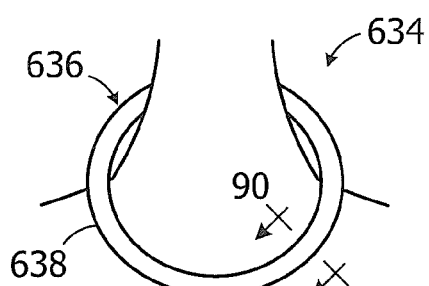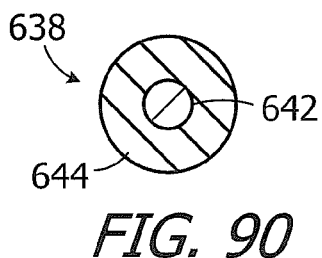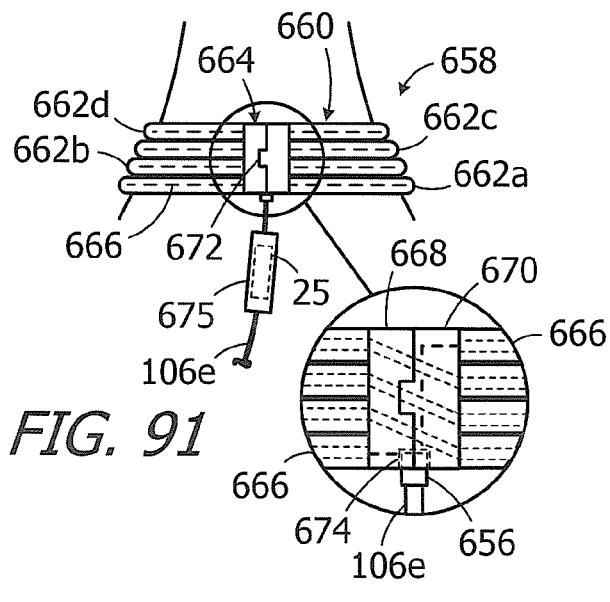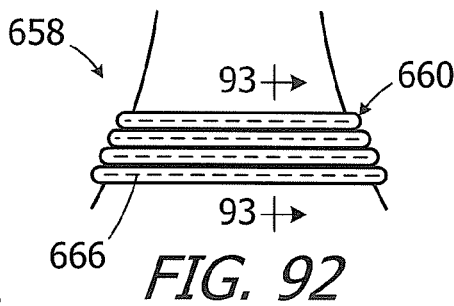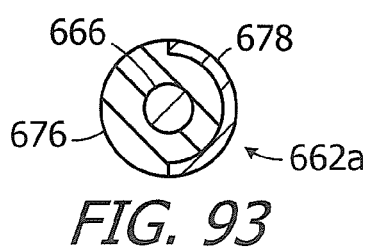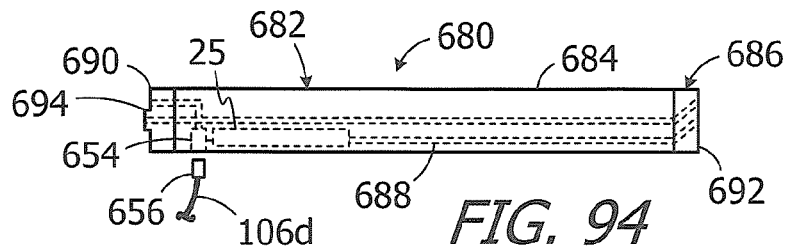

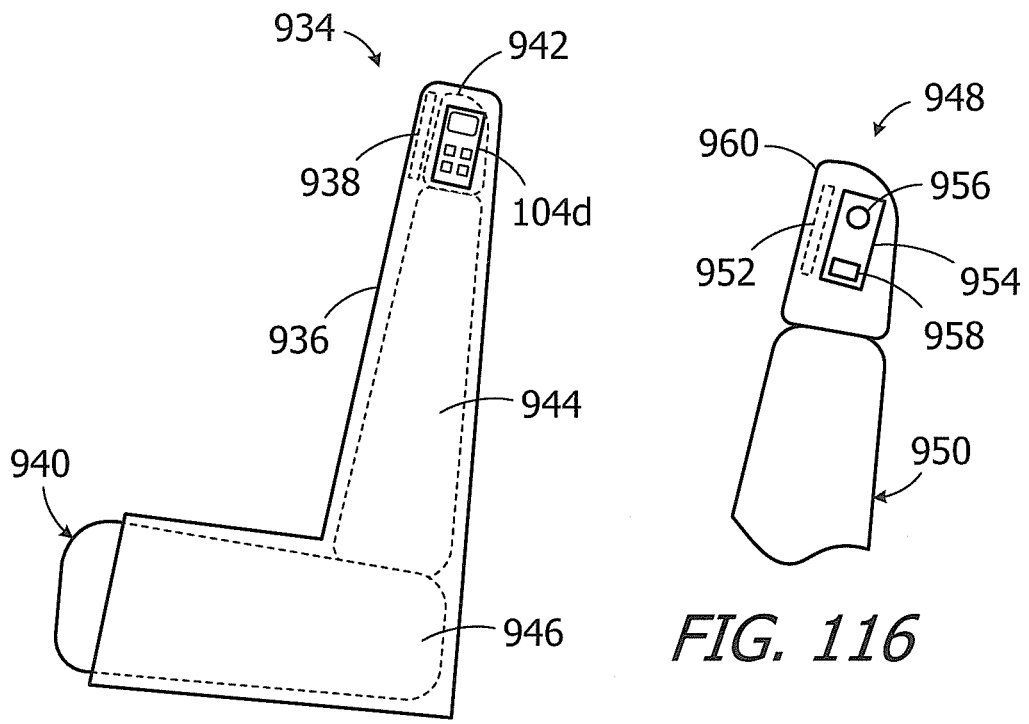
FIG. 115
FIG. 116
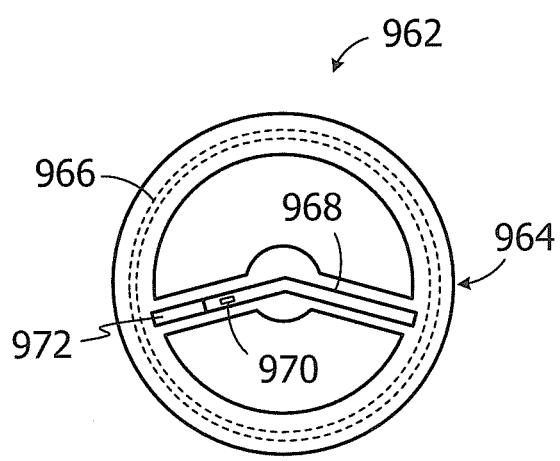
FIG. 117

APPARATUS AND METHODS FOR CHARGING AN IMPLANTED MEDICAL DEVICE POWER SOURCE

CROSS-REFERENCE TO RELATED APPLICATIONS

This application claims the benefit of and priority to previously filed U.S. Provisional Patent Application Ser. No. 60/974,062, filed Sep. 20, 2007, which is entitled "Apparatus and Methods For Charging An Implanted Medical Device Power Source" and incorporated herein by reference in its entirety.

BACKGROUND OF THE INVENTIONS

1. Field of Inventions

The present inventions relate generally to apparatus and methods for charging the rechargeable batteries (and/or other rechargeable power sources) in implanted medical devices.

2. Description of the Related Art

A variety of power consuming medical devices may be implanted into a patient. Examples of such implantable medical devices include, but are not limited to, microstimulators (e.g. occipital nerve stimulators, vagus nerve stimulators, and stimulators that may be positioned at various locations to treat rheumatoid arthritis), implantable pulse generators, drug infusion pumps, speech processors, pacemakers and defibrillators. In addition to their therapeutic and/or diagnostic components, the implantable medical devices include rechargeable power sources such as rechargeable batteries, capacitors, and combinations thereof. The length of time that an implantable medical device can operate between chargings of the rechargeable power source varies from device to device. For example, pacemaker batteries may only need to be recharged every few years, while microstimulators (e.g. an occipital nerve stimulator) may need to be recharged several times a day.

The present inventors have determined that conventional methods and apparatus for charging the rechargeable power sources in implanted medical devices are susceptible to improvement. For example, the present inventors have determined that conventional methods and apparatus for charging the rechargeable power sources can involve the use of large and bulky chargers that are difficult to incorporate into daily life. The present inventors have also determined that it can be difficult to maintain the proper position of conventional chargers on the body relative to the implanted medical device.

SUMMARY OF THE INVENTIONS

Apparatus and methods in accordance with one of the present inventions include, and/or involve the use of, an inductor and a fastener apparatus configured to removably secure the inductor to a wearable device.

Apparatus and methods in accordance with one of the present inventions include, and/or involve the use of, a wearable device and an inductor permanently associated with the wearable device.

Apparatus and methods in accordance with one of the present inventions include, and/or involve the use of, an implanted medical device charger and a mounting apparatus configured to removably mount the implanted medical device charger on an article of clothing.

Apparatus and methods in accordance with one of the present inventions include, and/or involve the use of, an implanted medical device charger and a mounting apparatus configured to removably mount the implanted medical device charger on the torso of a wearer.

Apparatus and methods in accordance with one of the present inventions include, and/or involve the use of, a non-wearable device having utility beyond implanted medical device charging and an inductor associated with the non-wearable device.

Such apparatus and methods are advantageous for a variety of reasons. For example, the apparatus and methods provide a convenient way to incorporate the charging of an implanted medical device into daily life and to maintain the proper position of a charging inductor (or an entire charger) on or near the body relative to the implanted medical device.

The above described and many other features of the present inventions will become apparent as the inventions become better understood by reference to the following detailed description when considered in conjunction with the accompanying drawings.

BRIEF DESCRIPTION OF THE DRAWINGS

Detailed description of exemplary embodiments of the inventions will be made with reference to the accompanying drawings.

FIG. 2A is a side view of an inductor in accordance with one embodiment of a present invention.

FIG. 2B is a side view of an inductor in accordance with one embodiment of a present invention.

FIG. 2C is a plan view of an inductor in accordance with one embodiment of a present invention.

FIG. 2D is a side view of the inductor illustrated in FIG. 2C.

FIG. 3 is a front view of a charging appliance in accordance with one embodiment of a present invention secured to a shirt collar.

FIG. 4 is a side view of a portion of the charging appliance illustrated in FIG. 3.

FIG. 5 is a plan view of a portion of the charging appliance illustrated in FIG. 3.

FIG. 6 is a plan view of a portion of the charging appliance illustrated in FIG. 3.

FIG. 13 is a side view showing the charging appliance illustrated in FIG. 3 secured to a helmet.

FIG. 14 is a perspective view showing the charging appliance illustrated in FIG. 3 secured to a helmet.

FIG. 15 is a plan view showing the charging appliance illustrated in FIG. 3 secured to a belt.

FIG. 16 is a plan view showing the charging appliance illustrated in FIG. 3 secured to a heart rate monitor.

FIG. 17 is a front view showing the charging appliance illustrated in FIG. 3 secured to a knee brace.

FIG. 42 is a front perspective view of a charging appliance in accordance with one embodiment of a present invention.

FIG. 43 is a rear perspective view of the charging appliance illustrated in FIG. 42.

FIG. 44 is a front perspective view of a charging appliance in accordance with one embodiment of a present invention.

FIG. 45 is a rear perspective view of the charging appliance illustrated in FIG. 44.

FIG. 46 is a front perspective view of a charging appliance in accordance with one embodiment of a present invention.

FIG. 67 is a front view of a charging appliance in accordance with one embodiment of a present invention.

FIG. 68 is a bottom view of a portion of the charging appliance illustrated in FIG. 67.

FIG. 69 is a plan view of a charging appliance in accordance with one embodiment of a present invention.

FIG. 70 is a plan view of a charging appliance in accordance with one embodiment of a present invention.

FIG. 71 is a front view of a charging appliance in accordance with one embodiment of a present invention.

FIG. 72 is a plan view of a charging appliance in accordance with one embodiment of a present invention.

FIG. 73 is a front view of a charging appliance in accordance with one embodiment of a present invention.

FIG. 74 is a front view of a charging appliance in accordance with one embodiment of a present invention.

FIG. 75 is a front view of a charging appliance in accordance with one embodiment of a present invention.

FIG. 76 is a bottom view of a portion of the charging appliance illustrated in FIG. 75.

FIG. 77 is a front view of a charging appliance in accordance with one embodiment of a present invention.

FIG. 78 is a bottom view of a portion of the charging appliance illustrated in FIG. 77.

FIG. 79 is a perspective view of a charging appliance in accordance with one embodiment of a present invention.

FIG. 80 is a perspective view of a charging appliance in accordance with one embodiment of a present invention.

FIG. 88 is a rear view of a charging appliance in accordance with one embodiment of a present invention.

FIG. 89 is a front view of a portion of the charging appliance illustrated in FIG. 88.

FIG. 90 is a section view taken along line 90-90 in FIG. 89.

FIG. 91 is a rear view of a charging appliance in accordance with one embodiment of a present invention.

FIG. 92 is a front view of a portion of the charging appliance illustrated in FIG. 91.

FIG. 93 is a section view taken along line 93-93 in FIG. 92.

FIG. 94 is a plan view of a charging appliance in accordance with one embodiment of a present invention.

FIG. 109 is a rear exploded view of a portion of the charging appliance illustrated in FIG. 108.

FIG. 110 is a front view of a charging appliance in accordance with one embodiment of a present invention.

FIG. 111 is a top plan view of a charging appliance in accordance with one embodiment of a present invention.

FIG. 112 is a bottom plan view of a portion of the charging appliance illustrated in FIG. 111.

FIG. 113 is a front view of a charging appliance in accordance with one embodiment of a present invention.

FIG. 114 is a rear view of the charging appliance illustrated in FIG. 113.

FIG. 115 is a side view of a charging appliance in accordance with one embodiment of a present invention.

FIG. 116 is a side view of a portion of a charging appliance in accordance with one embodiment of a present invention.

FIG. 117 is a plan view of a charging appliance in accordance with one embodiment of a present invention.

DETAILED DESCRIPTION OF THE EXEMPLARY EMBODIMENTS

The following is a detailed description of the best presently known modes of carrying out the inventions. This description is not to be taken in a limiting sense, but is made merely for the purpose of illustrating the general principles of the inventions. The detailed description is organized as follows:

I. Overview
II. Exemplary Charging Appliances That May Be Associated With Wearable Devices
III. Charging Appliances That May Be Associated With Non-Wearable Devices The section titles and overall organization of the present detailed description are for the purpose of convenience only and are not intended to limit the present inventions.

I. Overview

Figure 1A:
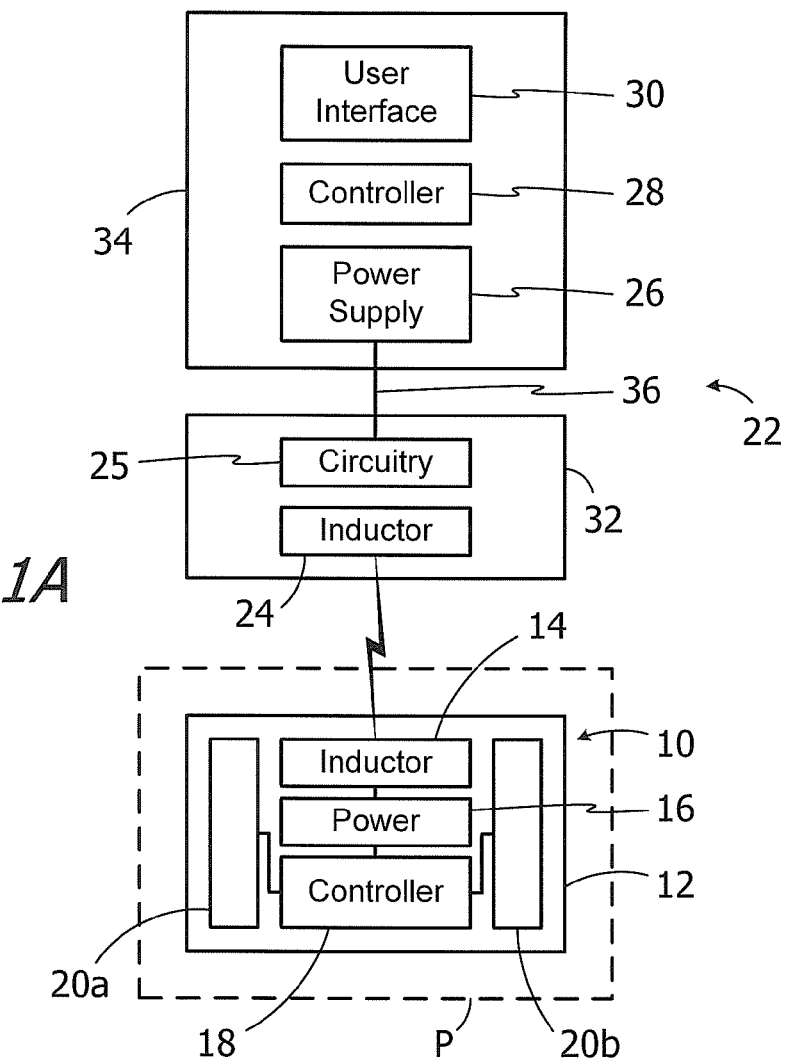
FIG. 1A is a functional block diagram of a medical device and a charging appliance in accordance with one embodiment of a present invention.

As illustrated in FIG. 1A, a medical device 10, having an external housing 12, an internal inductor 14 (e.g. a conductive coil and a core of air or a ferromagnetic material), a rechargeable power source 16, and power consuming apparatus (e.g. a controller 18 and electrodes or other therapeutic devices 20a and 20b), may be implanted in a patient P. Examples of medical devices that may be implanted into a patient include, but are not limited to, occipital nerve stimulators, such as that illustrated in U.S. Pat. No. 6,735,474, other microstimulators, implantable pulse generators, drug infusion pumps, speech processors, pacemakers and defibrillators. The power source 16 in the medical device 10 may be charged with a charging appliance 22.

The exemplary charging appliance 22, all or part of which may be positioned on or near the patient in close proximity to the implanted medical device 10, includes one or more inductors 24 (herein after "inductor"), inductor related circuitry 25 (e.g. tuning capacitors, switches and temperature sensors), a power supply 26 (e.g. a primary battery, a replenishable or rechargeable battery such as a lithium ion battery, an electrolytic capacitor, a super- or ultra-capacitor, or some other power supply), a controller 28 and a user interface 30. In those instances where the power supply is replenishable or rechargeable, apparatus for replenishing or recharging the power source (e.g., an RF link, an optical link, a thermal link, or other energy-coupling link, may be provided. The user interface 30 may consist of any suitable instrumentality including, for example, one or more buttons, a touch screen, one or more LEDs (or other visible indicators), and a buzzer (or other sound emitting device) or a vibrating mechanism. The power source 16 in the implanted medical device 10 may be charged by transferring power from the power supply 26 to the implanted power source 16 by way of the inductors 14 and 24.

As is described in greater detail below, the charging appliance 22 (or at least a portion thereof) may be carried by, part of, secured to and/or otherwise related to an apparatus that is associated with the patient's everyday life. For example, and referring to FIG. 1A, the inductor 24 and inductor related circuitry 25 may be incorporated into a device 32 that is carried by, part of, or secured to an apparatus that is associated with the patient's everyday life, while the power supply 26, controller 28, and user interface 30 will be included in a remote housing 34 that is connected to the inductor 24 by a cable 36 with an output line and a return line. The cable connection may, however, be replaced by wireless connection in the embodiment illustrated in FIG. 1A and in each of the embodiments described below that includes a cable connection. Alternatively, in the exemplary charging appliance 22a illustrated in FIG. 1B, the inductor 24, inductor related circuitry 25, power supply 26, controller 28, and user interface 30 may be part of the same device 32a, which has a single common housing and may be carried by, part of, or secured to an apparatus that is associated with the patient's everyday life.

The actual position of the inductor will depend on the location of the implanted medical device. An inductor that is positioned adjacent to the back of the neck may be used, for example, to charge the power source in an occipital nerve stimulator or an implantable pulse generator (IPG) with one or more leads for trigeminal nerve stimulation or deep brain stimulation. An inductor that is positioned near the front or side portion of the neck may be used, for example, to charge the power source in a vagus nerve stimulator. An inductor that is positioned on or behind the ear may be used, for example, to charge the power source in an IPG with one or more leads (e.g. for trigeminal nerve stimulation) implanted behind ear or to charge the power source in a cochlear implant, while an inductor that is positioned on or in front of the ear may be used, for example, to charge the power source in an auriculotemporal nerve stimulator. Inductors that are positioned on or adjacent to the chin or forehead may be used, for example, to charge the power source in a trigeminal nerve stimulator. Inductors that are positioned at various locations around the waist may be used, for example, to charge the power source in an ilioinguinal nerve stimulator or the power source in an IPG that is mounted at or near buttocks with leads that may be used in any of a wide variety of stimulation therapies. An inductor that is positioned just below the chest may be used, for example, to charge the power source in an intercostal nerve stimulator or the power source in a phrenic nerve stimulator. Inductors that are positioned on or adjacent to other portions of the torso (e.g. beneath the axilla, on the upper chest near the shoulder, or in the mid-back area) may be used, for example, to charge the power source in an IPG with one or more leads for spinal cord stimulation, occipital nerve stimulation, deep brain stimulation, or to charge the power source in a stimulator implanted to treat post thoracotomy pain. Inductors that are positioned on or adjacent to joints (e.g. the knee or the wrist) may be used, for example, to charge the power sources in stimulators that treat rheumatoid arthritis. An inductor that is positioned on or adjacent to the pelvic region may be used, for example, to charge the power source in a pudendal nerve stimulator.

It should also be noted that a wide variety of inductors 24 may be employed. By way of example, the inductor 24a illustrated in FIG. 2A includes a coil 38 and a ferromagnetic core 40, while the inductor 24b illustrated in FIG. 2B includes the coil 38 and an air core. Turning to FIG. 2C, the inductor 24c includes a relatively flat, tightly wound coil 42 and a ferromagnetic core 44. In each instance, the dimensions of the inductor may depend on the dimensions of the underlying charging appliance. For example, the inductor 24c may have a relatively small diameter in some of the embodiments described below and a relatively large diameter in others.

II. Charging Appliances that May be Associated with Wearable Devices

Wearable devices are one example of apparatus that charging appliances may be carried by, part of, secured to and/or otherwise associated with. As used herein, a "wearable device" refers to all clothing (or "garments"), clothing clasps, costumes, harnesses, jewelry, piercings, hats and other head coverings, eye glasses, uniforms, sporting goods that are carried by the body or are otherwise worn, prosthetics, footwear and shoe inserts, protective gear, bags (e.g. a backpack or purse), externally worn medical devices and externally worn non-medical electronic devices (e.g. headphones). Regardless of the type of wearable device, the wearable device and charging appliance will cooperatively position the associated inductor in close proximity to the implanted medical device to facilitate charging in, for example, the manner described above with reference to FIG. 1A.

As illustrated in FIGS. 3-6, an exemplary charging appliance 100 includes a magnetic clasp 102 that carries one or more inductors and inductor related circuitry (e.g. inductor 24c and related circuitry 25) and a remote housing 104 that carries the power supply and control apparatus (e.g. the power supply 26, controller 28 and user interface 30). A cable 106 connects the inductor and inductor related circuitry carried by the magnetic clasp 102 to the power supply and control apparatus carried by the remote housing 104. The cable 106 may be replaced by wireless connection in the embodiment illustrated in FIGS. 3-6 and in each of the embodiments described below that includes a cable connection. The magnetic clasp 102 may be secured to a shirt or blouse collar 108, any other garment or portion thereof, or any other wearable device, while the remote housing 104 includes a clip 110 that allows the remote housing to be mounted on, for example, a belt or other article of clothing.

The exemplary magnetic clasp 102 in the illustrated embodiment has a main portion 112, which includes the inductor 24c and related circuitry 25, and a backing 114, which cooperates with the main portion to secure the magnetic clasp to the collar 108. The inductor 24c and inductor related circuitry 25 may be molded into an epoxy, silicone, or urethane structure that is carried within a plastic case 116, thereby electrically insulating the main portion 112 from the wearer. Alternatively, the inductor 24c and inductor related circuitry 25 may be carried within a polycarbonate case, that is itself coated with an insulating encapsulate such as silicone, rubber-like polymers, Teflon, and other plastics. Here too, the main portion 112 will be electrically insulated from the wearer. Turning to the backing, the exemplary backing 114 consists of a magnet 118 that is carried within a plastic housing 120 and attracted to the ferromagnetic core 44 of the inductor 24c. The backing may, alternatively, consist solely of a magnet.

The magnetic clasp 102 may, in some implementations, be provided with apparatus that centers the main portion 112 relative to the backing 114. In the exemplary implementation illustrated in FIGS. 3-6, the main portion 112 includes a post 122 that is configured to pass through the associated article of clothing (i.e. is relatively sharp and thin) and the backing 114 includes an aperture 124 that is configured to receive the post. It should also be noted here that the main portion and the backing may, alternatively, be secured to one another through the use of non-magnetic instrumentalities, such as a snap, a button or thread, and that the backing 114 may be omitted and the main portion 112 secured to a garment or other wearable device with pins, hooks, buttons, clasps, buckles, clips, snaps or any other suitable mechanical fastener.

With respect to use, and as illustrated for example in FIG. 3, the main portion 112 of the exemplary magnetic clasp 102 may be placed on the inner surface of the collar 108, so that the inductor 24c is close to the implanted medical device, while the backing 114 may be placed on the outer surface of the collar under the collar flap. As a result, the cable 106 will be located within the shirt or blouse and the charging appliance 100 will be completely, or almost completely depending on the location of the remote housing 104, out of sight. The wearer may then charge the power source of the implanted medical device by operating the user interface on the remote housing 104 (e.g. by pressing a button). The locations of the main portion 112 and backing 114 may also be reversed, so that the cable 106 will be located on the outside of the shirt or blouse, if so desired.

Figure 7:
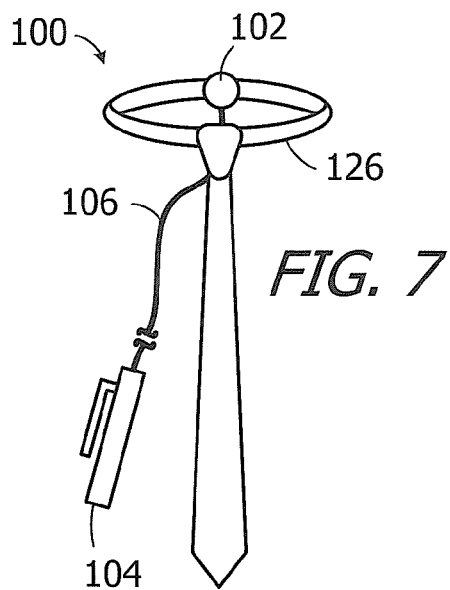
FIG. 7 is a front view showing the charging appliance illustrated in FIG. 3 secured to a necktie.
Figure 8:
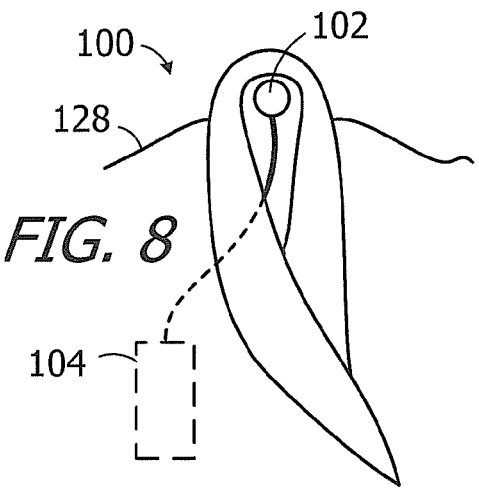
FIG. 8 is a front view showing the charging appliance illustrated in FIG. 3 secured to a coat collar.
Figure 9:
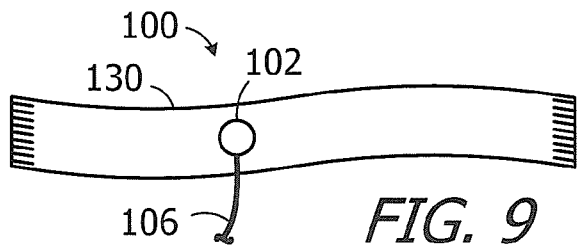
FIG. 9 is a front view showing the charging appliance illustrated in FIG. 3 secured to a scarf.
Figure 10:
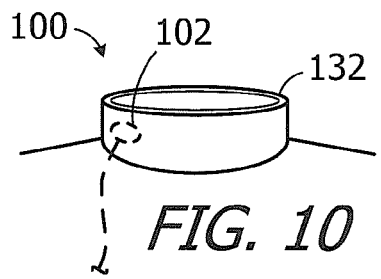
FIG. 10 is a front view showing the charging appliance illustrated in FIG. 3 secured to a turtleneck collar.

The charging appliance 100 may, of course, be used in combination with a wide variety of garments. By way of example, but not limitation, the charging appliance 100 may be used in combination with necktie 126 (FIG. 7), a coat 128 (FIG. 8), a scarf 130 (FIG. 9), a turtleneck collar 132 (FIG. 10) so as to position an inductor adjacent to a medical device that is implanted within the neck.

Figure 11:
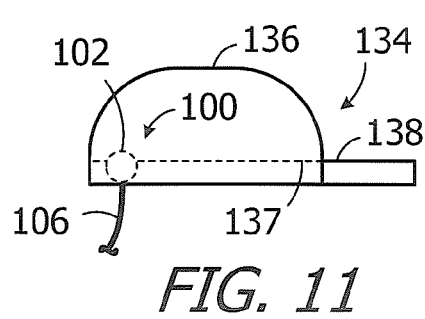
FIG. 11 is a side view showing the charging appliance illustrated in FIG. 3 secured to a hat.
Figure 12:
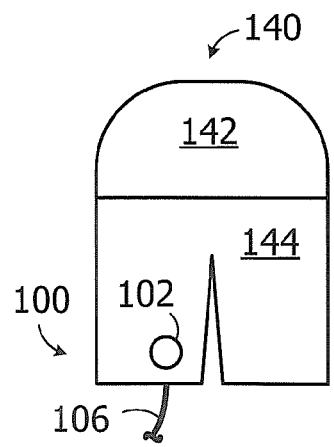
FIG. 12 is a rear view showing the charging appliance illustrated in FIG. 3 secured to a hat.

The charging appliance 100 may also be secured to caps, hats, helmets and other items that are typically worn on the head. One such hat, which is generally represented by reference numeral 134 in FIG. 11, includes a main portion 136, an inner rim 137 and a bill 138. The magnetic clasp 102 may be attached to any part of the main portion 136, the inner rim 137 (as shown), or the bill 138. Another exemplary hat is the safari hat 140 illustrated in FIG. 12, which includes a main portion 142, a bill (not shown), and flap 144 that shades the back of the neck. In addition to the main portion 142 and the bill, the magnetic clasp 102 may be attached to the flap 144 (as shown).

Turning to helmets, one example of a helmet to which the charging appliance 100 may be secured is the bicycle helmet 146 illustrated in FIG. 13, which includes a main portion 148 (e.g. a hard shell with an inner padded liner), a chin strap 150 and side straps 152 that are positioned in front of and behind the ear. The magnetic clasp 102 may be attached to the chin strap 150 (as shown), or to one of the side straps 152, or to the main portion 148. An exemplary equestrian helmet 154, which includes a main portion 156 (e.g. a hard shell with an inner padded liner), a chin strap 158 and side straps 160 that are positioned in front of and behind the ear, is illustrated in FIG. 14. Here too, the magnetic clasp 102 may be attached to the chin strap 158 or to one of the side straps 160 (as shown).

The charging appliance 100 may also be secured to belts and belt-like devices. Referring first to FIG. 15, the charging appliance 100 may be secured to a belt 162 that includes an elongate strap 164, which is sized to encircle the wearer's waist, and a mechanism to fasten one portion of the strap to another (e.g. the holes 166 and buckle 168). In the illustrated embodiment, the magnetic clasp 102 is secured to one portion of the elongate strap 164, while the clip 110 may be used to secure the remote housing 104 to another portion of the strap. A heart rate monitor 170 is one example of a belt-like device to which the charging appliance 100 may be secured. The exemplary heart rate monitor includes a sensor/display apparatus 172, an elongate strap 174 formed from an elastomeric material such as that sold under the trade name Neoprene, and a mechanism to fasten one portion of the strap to another such as hook and loop strips 176 and 178 (e.g. the fastener strips commonly sold under the trade name Velcro). Here, the magnetic clasp 102 is secured to the elongate strap 174. The heart rate monitor 170 will typically be positioned around the wearer's torso just below the chest. A similar constructed fetal monitor (not shown) is another example of a belt-like device to which the charging appliance 100 may be secured.

A joint brace, such as those commonly used to support the wrist, elbow, ankle or knee, is another example of a type of device to which the charging appliance 100 may be secured. Referring to FIG. 17, one specific example of a joint brace is the knee brace 180, which includes a cuff 182 formed from an elastomeric material such as that sold under the trade name Neoprene, an opening 184 for the wearer's patella, and adjustable straps 186.

Figure 1B:
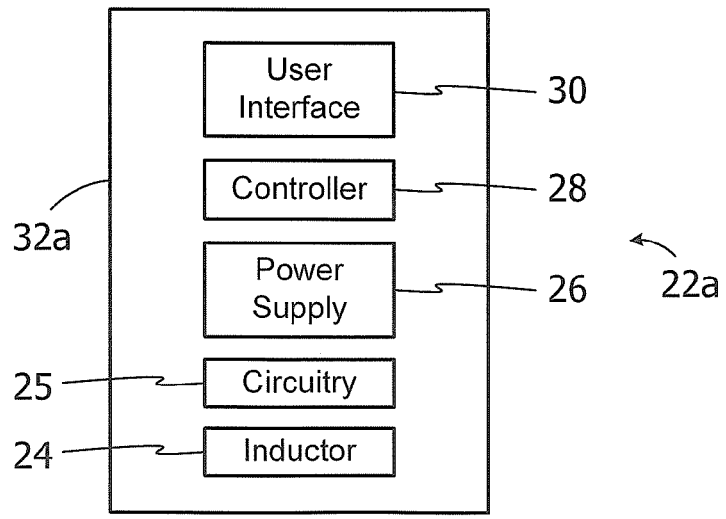
FIG. 1B is a functional block diagram of a charging appliance in accordance with one embodiment of a present invention.

The exemplary charging appliances illustrated in FIGS. 1A and 3-17 above and FIGS. 64-95 and 100 below include an inductor and inductor related circuitry which are located remotely from, and connected by a cable (or wireless connection) to, the user interface, controller and power supply. Other exemplary charging appliances, which are illustrated in FIG. 1B above and FIGS. 18-63 and 96-99 below include a charger with an inductor, inductor related circuitry, user interface, controller and power supply that are associated with a common housing or common overall device. The charger may be positioned adjacent to the implanted medical device, or part of the implanted medical device, in a variety of ways. For example, the charger may be secured to an article of clothing in such a manner that the article of clothing maintains the charger in the intended location. Alternatively, the charger may be carried by a wearable device that is configured to position the charger adjacent to an implanted medical device, or part of the implanted medical device, without the assistance of an article of clothing.

Figure 18:
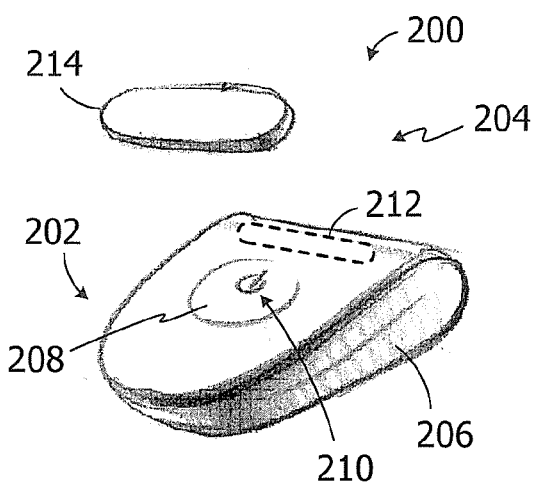
FIG. 18 is a perspective view of a charging appliance in accordance with one embodiment of a present invention.
Figure 19:
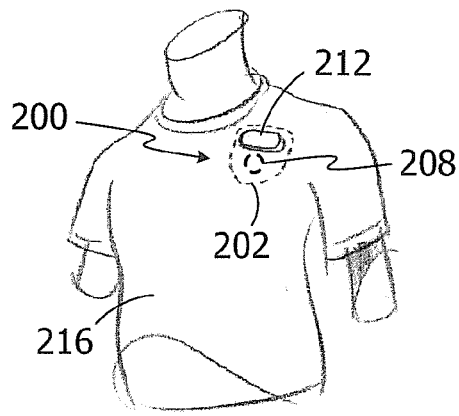
FIG. 19 is a perspective view showing the charging appliance illustrated in FIG. 18 secured to shirt.

One example of a charging appliance that is configured be secured to an article of clothing is generally represented by reference numeral 200 in FIGS. 18 and 19. The exemplary charging appliance 200 includes a charger 202 and a mounting apparatus 204 that may be used to secure the charger 202 to an article of clothing or other wearable device. The exemplary charger 202 has a housing 206 in which the inductor, inductor related circuitry, power supply, and controller are carried. The user interface is in the form of a button 208 and a light emitting element, such as an LED, that is visible through a slot 210 formed in the button. The mounting apparatus 204 in the exemplary charging appliance 200 includes a pair of magnets 212 and 214 that are attracted to one another. Magnet 212 is associated with the charger 202 and may be carried within the housing 206 (as shown) or secured to the exterior of the housing. Alternatively, the magnet 212 may be omitted and the magnet associated with the inductor, e.g. the magnets 40 and 44 illustrated in FIGS. 2A and 2C, used in its place.

The mounting apparatus 204 may be used to secure the charging appliance 200 to an article of clothing in, for example, the manner illustrated in FIG. 19. The article of clothing will, in turn, maintain the position of charging appliance 200 relative to the wearer generally, and the implanted medical device in particular. More specifically, the charger 202 may be positioned between a shirt 216 and the upper portion of the wearer's chest. The magnet 214 may then be positioned on the exterior of the shirt 216 in alignment with the magnet 212, thereby securing the charging apparatus 200 to the shirt. The button 208 may be pressed through the shirt 216 as desired to charge the associated implanted medical device.

Figure 20:
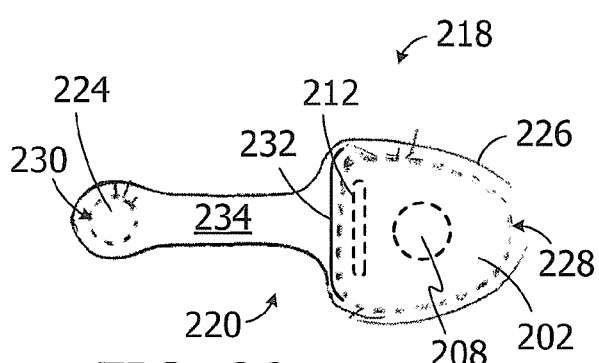
FIG. 20 is a plan view of a charging appliance in accordance with one embodiment of a present invention.
Figure 21:
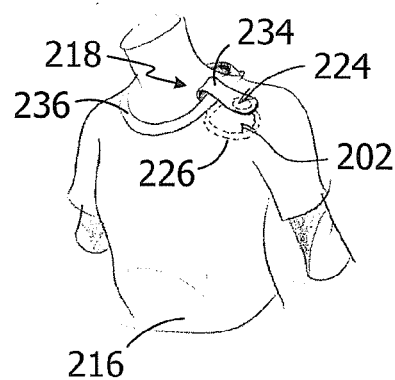
FIG. 21 is a perspective view showing the charging appliance illustrated in FIG. 20 secured to shirt.

Another exemplary charging appliance that may be secured to clothing is generally represented by reference numeral 218 in FIGS. 20 and 21. The exemplary charging appliance 218 includes the aforementioned charger 202 and a mounting apparatus 220. The mounting apparatus 220 includes a pair of magnets 212 and 224 that are attracted to one another, and a pouch 226 with pockets 228 and 230. The charger 202 may be removably positioned within pocket 228 and, to that end, the exterior of the pouch 226 includes a slit 232 which provides access to the pocket. Magnet 212 is associated with the charger 202 and may be carried within the charger housing (as shown) or secured to the exterior of the housing. Alternatively, the magnet 212 may be permanently or removably positioned within a pouch pocket. The magnet 212 may also be omitted and the magnet associated with the inductor, e.g. the magnets 40 and 44 illustrated in FIGS. 2A and 2C, used in its place. Magnet 224 may be permanently or removably positioned within pouch pocket 230. The portions of the pouch 226 that include the pockets 228 and 230 are connected to one another by a flexible hinge 234.

Suitable materials for the pouch 226 include, but are not limited to, synthetic textile materials such as that sold under the trade name Cambrelle, elastomeric material such as that sold under the trade name Neoprene, materials woven from fibers, such as those sold under the trade name Hydrofil, which include a water-absorbing component, and any combinations thereof. Such materials are also suitable for the pouches described below in the context of FIGS. 22-25, 28A-29E and 34.

The mounting apparatus 220 may be used to secure the charging appliance 218 to an article of clothing in, for example, the manner described below with reference to FIG. 21. The article of clothing will, in turn, maintain the position of charging appliance 218 relative to the wearer generally, and the implanted medical device in particular. Turning to FIG. 21, the charger 202 and associated portion of the pouch 226 may be positioned between the shirt 216 and the user's chest, and the flexible hinge 234 bent around the shirt collar 236 as shown. The user will then align the magnet 224 with the magnet 212, thereby securing the charging apparatus 218 to the shirt 216. The button 208 may then pressed through the shirt as desired to charge the associated implanted medical device.

Figure 22:
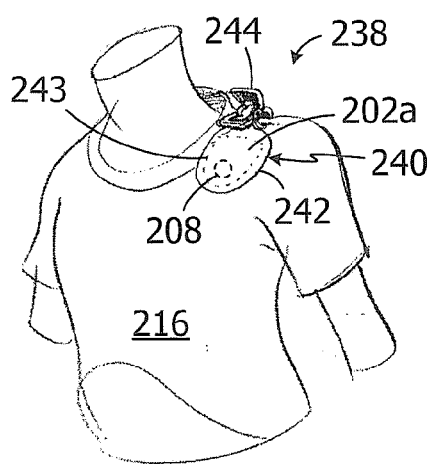
FIG. 22 is a perspective view showing a charging appliance in accordance with one embodiment of a present invention secured to shirt.
Figure 23:
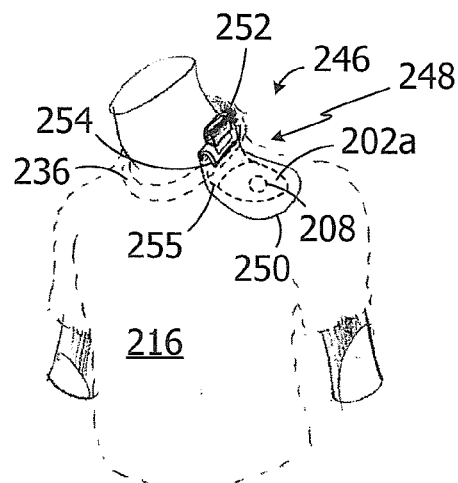
FIG. 23 is a perspective view showing a charging appliance in accordance with one embodiment of a present invention secured to shirt.
Figure 24:
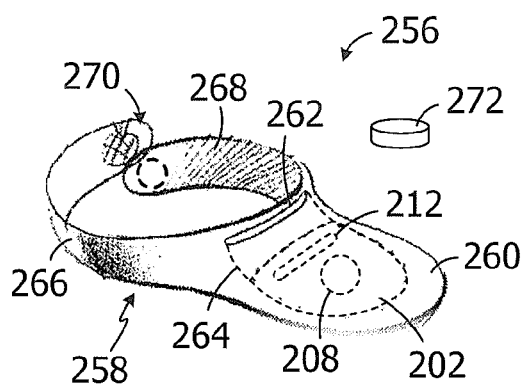
FIG. 24 is a perspective view of a charging appliance in accordance with one embodiment of a present invention.

Still other exemplary charging appliances which are configured to be secured to an article of clothing are illustrated in FIGS. 22 and 23. Here, the charging appliances employ a clip, pin, hook, clasp or other mechanical fastener to secure the charger to an article of clothing. Referring first to FIG. 22, the exemplary charging appliance 238 includes a charger 202a and a mounting apparatus 240. The exemplary charger 202a is identical to the charger 202, but for the absence of the magnet 212. Turning to the mounting apparatus, the exemplary mounting apparatus 240 includes a pouch 242 that carries the charger 202a and a clip 244 that secures the pouch to an article of clothing, such as the shirt 216. In the illustrated embodiment, the pouch has a slit or other opening on the side that is not visible in FIG. 22, which allows the charger 202a inserted into, and removed from, a pouch pocket 243. The clip 244 is biased to the closed orientation illustrated in FIG. 22. The respective configurations of the pouch 242 and clip 244, as well as the manner in which the pouch and clip are secured to one another, will typically result in charging appliance 238 being positioned on the exterior of the associated article of clothing.

Turning to FIG. 23, the exemplary charging appliance 246 is configured such that one portion will be located on the exterior of the associated article of clothing (e.g. the shirt 216) and another portion will be located between the wearer and the article of clothing. More specifically, the exemplary charging appliance 246 includes the charger 202a and a mounting apparatus 248. The exemplary mounting apparatus 248 includes a pouch 250 that carries the charger 202a and a clip 252 that secures the pouch to a portion of an article of clothing, such as the collar 236 of the shirt 216. In the illustrated embodiment, the pouch 250 has a slit or other opening (not shown) under a flap 254, which facilitates the insertion and removal of the charger 202a from the pouch pocket 255. The clip 252 is secured to the flap and is biased to the closed orientation illustrated in FIG. 23. The respective configurations of the pouch 250 and clip 252, as well as the manner in which the pouch and clip are secured to one another, allows the clip to secure a portion of the pouch flap 254 to the shirt collar 236 while the charger 202a and remainder of the pouch is located under the shirt 216.

Charging appliances may also be configured such that they may be secured both to the wearer and to an article of clothing. One example of such a charging appliance is generally represented by reference numeral 256 in FIGS. 24 and 25. The exemplary charging appliance 256 includes the above-described charger 202 and a mounting apparatus 258 that carries the charger 202 and is configured to secure the charger to both the wearer and to an article of clothing. To that end, the mounting apparatus 258 includes a pouch 260 with a slot 262 which allows the charger 202 to be inserted into and removed from a pocket 264, a pair of straps 266 and 268 that extend from the pouch, fasteners 270 (e.g. hook and loop fasteners) associated with the ends of the straps opposite pouch, and a pair of magnets 212 and 272 that are attracted to one another. Although the magnet 212 is located within the charger housing in the illustrated embodiment, in other embodiments it may be secured to the exterior of the charger housing, carried by the pouch 260, or simply omitted and replaced functionally by the magnet associated with the charger inductor.

Figure 25:
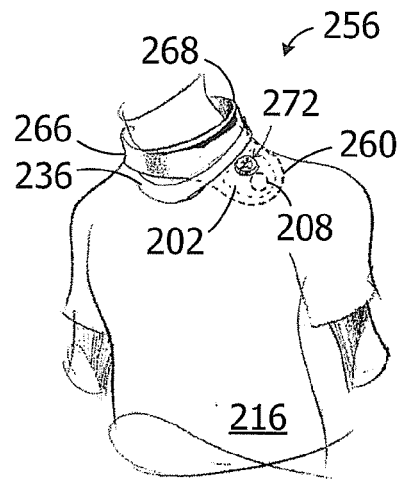
FIG. 25 is a perspective view showing the charging appliance illustrated in FIG. 24 secured to shirt.

The mounting apparatus 258 may be used to secure the charging appliance 256 to an anchoring location on the wearer's body and to an article of clothing in, for example, the manner illustrated in FIG. 25. The wearer's body and the article of clothing will, in turn, maintain the position of charger 202 relative to the wearer generally, and the implanted medical device in particular. More specifically, the charger 202 and pouch 260 may be positioned between a shirt 216 and the wearer's upper chest area such that the straps 266 and 268 extend out from under the shirt collar 236. The straps 266 and 268 may then be positioned around the wearer's neck and secured to one another with the fastener 270. The magnet 272 may then be positioned on the exterior of the shirt 216 in alignment with the magnet 212, thereby securing the charging appliance 256 to the shirt.

Figure 26:
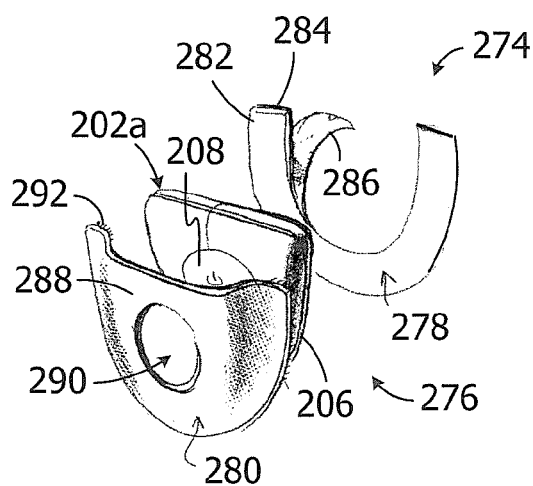
FIG. 26 is an exploded view of a charging appliance in accordance with one embodiment of a present invention.

Other charging appliances may be configured such that the mounting apparatus, or at least a portion thereof, is a permanent part of an otherwise conventional article of clothing. One example of such a charging appliance is generally represented by reference numeral 274 in FIGS. 26 and 27. Referring first to FIG. 26, the exemplary charging appliance 274 includes the above-described charger 202a and a mounting apparatus 276 that mounts the charger on an article of clothing. The mounting apparatus 276 is a two-part structure which consists of a base 278 that may be secured to the article of clothing and a cover 280 that may be secured to the base with the charger 202a therebetween. To that end, the exemplary base 278 consists of a U-shaped length of fastener material 282 (e.g. hook or loop material) with an adhesive backing 284. Suitable adhesives for the backing 284 include pressure sensitive adhesives and heat activated adhesives. A release liner 286 may also be provided. The cover 280 includes an indentation 288 that is configured to snuggly receive the charger 202a, an aperture 290 for the charger button 208, and U-shaped length of fastener material 292 (e.g. hook or loop material) with the same size and shape as the U-shaped length of fastener material 282. Suitable materials for the cover 280 include, but are not limited to, synthetic textile materials such as that sold under the trade name Cambrelle, elastomeric material such as that sold under the trade name Neoprene, materials woven from fibers, such as those sold under the trade name Hydrofil, which include a water-absorbing component, fabrics with moisture management aspects such as those sold under the trade name Dri-Lex (e.g. Dri-Lex 1230, Dri-Lex 2000, and Dri-Lex Fantasia), and any combinations thereof.

It should also be noted that, in other implementations, the adhesive backing 284 may be omitted and the base 278 attached to the article of clothing with stitches. Moreover, buttons, snaps, and other mechanical fasteners may be substituted for the faster material 282 and 292.

Figure 27:
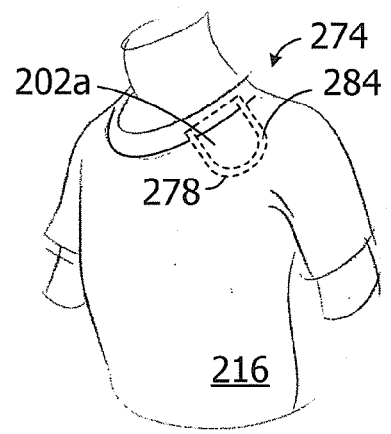
FIG. 27 is a perspective view showing the charging appliance illustrated in FIG. 26 secured to shirt.

Turning to FIG. 27, the adhesive backing 284 may be used to permanently secure the base 278 to the interior surface of the shirt 216, thereby rendering the shirt ready to receive the charger 202a and cover 280. Typically, the user will position the charger 202a within the indentation 288 (note FIG. 26), align the cover 280 with the base 278, and then secure the cover to the base with the U-shaped lengths of fastener material 282 and 292, thereby securing the charging appliance 274 to the shirt 216. The charger button 208 may be pressed before or after the charging appliance 274 is secured to the shirt.

Although the charging appliance 274 is secured to the upper chest portion of the shirt 216 in the illustrated embodiment, the location may be varied as necessitated by the location of the implanted medical device. The charging appliance 274 may also be associated with the exterior of the shirt 216 or other article of clothing. It should be noted that, in some instances, it is desirable to position the inductor within the charger as closed as practicable to the patient's skin. The charger 202a may, in such instances, be positioned such that the side of the charger housing 206 opposite the button 208 faces the aperture 290 when the mounting apparatus 276 is located on the inner surface of the shirt. The button 208 will face the shirt 216 through the base 278, and be pressed through the shirt.

Figure 28A:
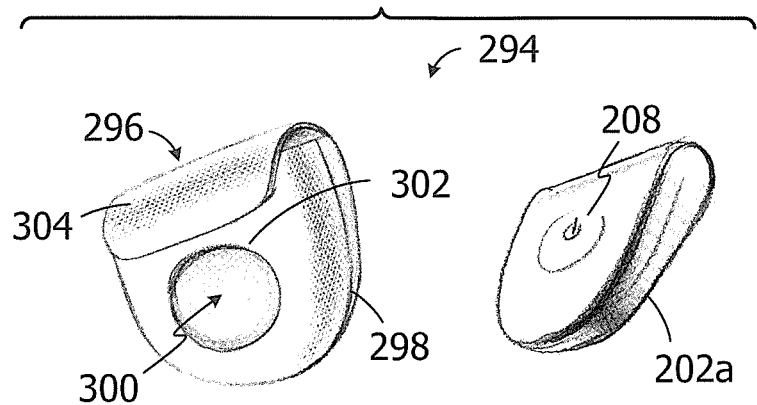
FIG. 28A is a perspective view of a charging appliance in accordance with one embodiment of a present invention.
Figure 28B:
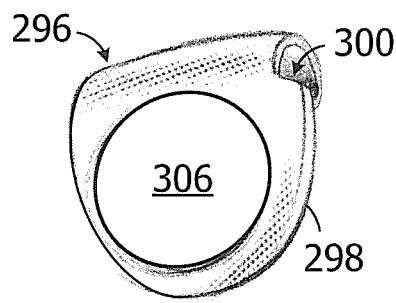
FIG. 28B is rear perspective view of the mounting apparatus illustrated in FIG. 28A.
Figure 28C:
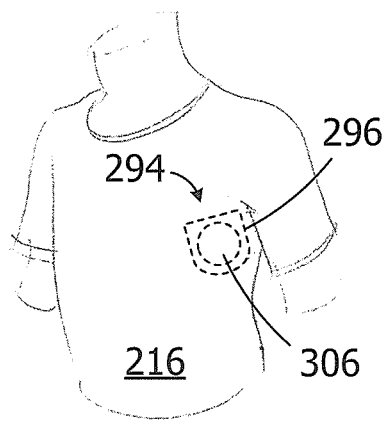
FIG. 28C is a perspective view showing the charging appliance illustrated in FIG. 28A secured to shirt.

One example of a charging appliance with a mounting apparatus that is a permanent part of an otherwise conventional article of clothing is generally represented by reference numeral 294 in FIGS. 28A and 28C. The exemplary charging appliance 294 includes the above-described charger 202a and a mounting apparatus 296 that mounts the charger on an article of clothing. Here, the mounting apparatus consists of a pouch 298, with a pocket 300 for the charger 202a, a front aperture 302, a flap 304, and an adhesive backing 306 (FIG. 28B) on the back of the pouch. As noted above, depending on the orientation of the charger 202a, the front aperture 302 either allows the charger button 208 to been observed and pressed, or facilitates placement of the charger inductor as close as practicable to the patient's skin. Suitable adhesives for the backing 306 include pressure sensitive adhesives and heat activated adhesives. A release liner (not shown) may also be provided.

As illustrated for example in FIG. 28C, the adhesive backing 306 may be used to permanently secure pouch 298 to the inner surface of the shirt 216. The charger 202a may be inserted into, and removed from, the pouch pocket 300 as desired. The pouch may also be secured to any other location on the interior or exterior of the shirt. It should also be noted that the pouch 296, as well as the pouches 296a-296c described below, may be permanently or temporarily secured to any other article of clothing (e.g. pants) required to position a charger adjacent to an implanted medical device.

Figure 29A:
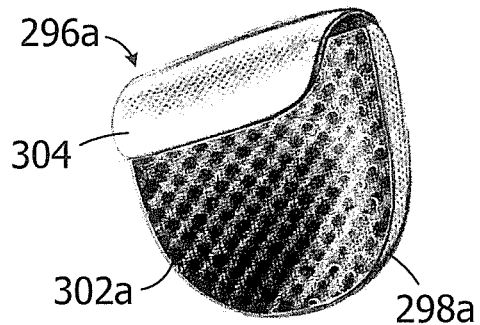
FIG. 29A is a front perspective view of a mounting apparatus in accordance with one embodiment of a present invention.
Figure 29B:
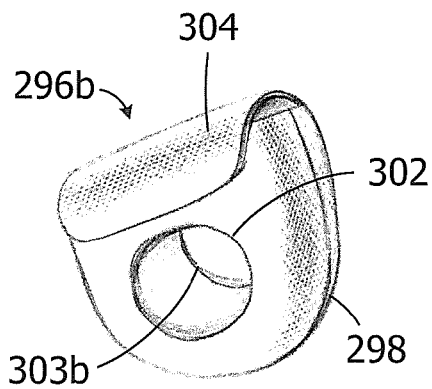
FIG. 29B is a front perspective view of a mounting apparatus in accordance with one embodiment of a present invention.
Figure 29C:
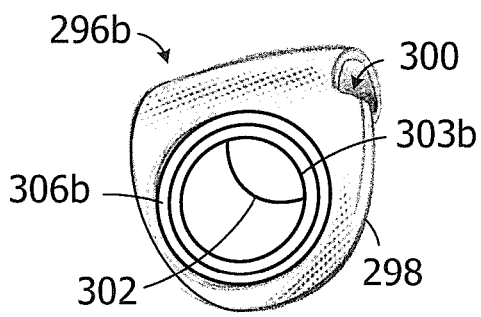
FIG. 29C is rear perspective view of the mounting apparatus illustrated in FIG. 29B.
Figure 29D:
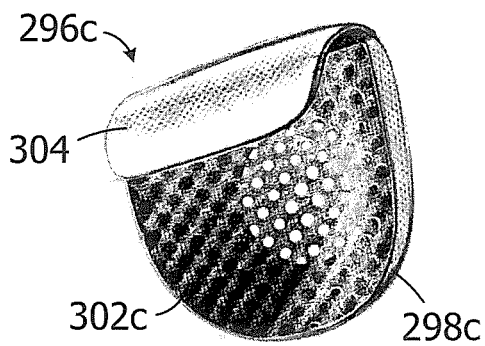
FIG. 29D is a front perspective view of a mounting apparatus in accordance with one embodiment of a present invention.
Figure 29E:
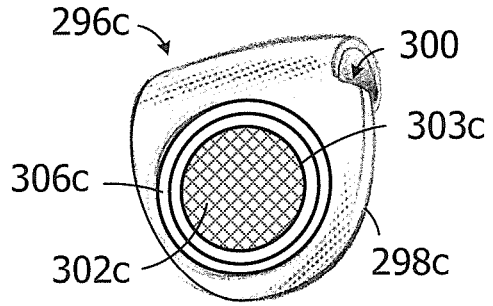
FIG. 29E is rear perspective view of the mounting apparatus illustrated in FIG. 29D.
Figure 30:
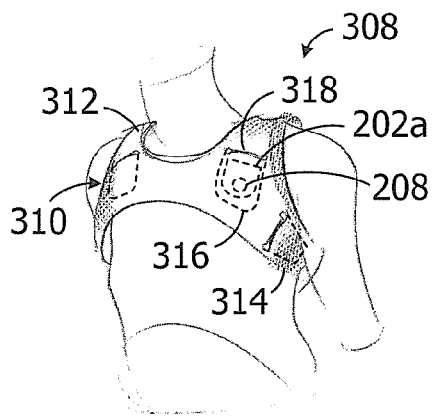
FIG. 30 is a front perspective view of a charging appliance in accordance with one embodiment of a present invention.
Figure 31:
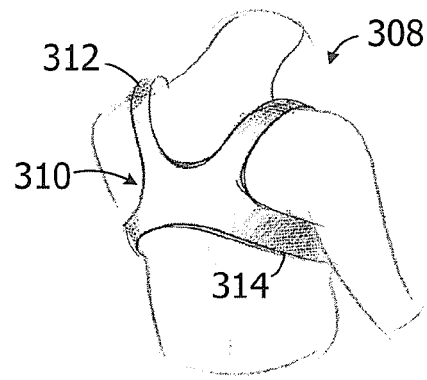
FIG. 31 is a rear perspective view of the charging appliance illustrated in FIG. 30.

A variety of other mounting apparatus may also be employed in place of the mounting apparatus 296. By way of example, but not limitation, the mounting apparatus 296a illustrated in FIG. 29A is substantially similar to the mounting apparatus 296 illustrated in FIGS. 28A-28C and similar elements are represented by similar reference numerals. Here, however, the front portion of pouch 298a is formed from soft mesh material 302a, such as the mesh material sold by Novatex International under the trade name Super Mesh. Like the front opening 302, the soft mesh material allows the charger button to observed and pressed. Adhesive (not shown) is provided on the rear side of the pouch 298a. Turning to FIGS. 29B and 29C, the exemplary mounting apparatus 296b is also substantially similar to the mounting apparatus 296 illustrated in FIGS. 28A-28C and similar elements are represented by similar reference numerals. Here, however, the pouch 298b includes a rear aperture 303b in addition to the front aperture 302. The adhesive backing 306b is annularly shaped in order to accommodate the rear aperture 303b. Another exemplary mounting apparatus, which is generally represented by reference numeral 296c in FIGS. 29D and 29E, includes a pouch 298c with a front portion formed from soft mesh material 302c and a rear aperture 303c. An annularly shaped adhesive backing 306c is positioned around the rear aperture 303c. Other exemplary mounting apparatus include pouches similar to pouch 298, but without an aperture, and pouches formed entirely from soft mesh material.

Still other charging appliances may be configured to be secured to, or otherwise carried by, the wearer's body in such a manner that the associated charger will be aligned with an implanted medical device. Such charging appliances may be worn under, over, or in the absence of conventional articles of clothing. One such charging appliance is generally represented by reference numeral 308 in FIGS. 30 and 31. The exemplary charging appliance 308 includes the charger 202a and a shoulder harness 310 that is configured to mount the charger in a plurality of different locations relative to the wearer. To that end, the exemplary shoulder harness includes a pair of shoulder straps 312 and a pair of chest straps 314 that are connected to one another as shown to form an integral unit, and a plurality of pockets 316 with exterior openings 318 that are configured to receive the charger 202a. The pockets 316 can extend in one direction from the openings 318 (as shown), or in two directions. Additionally, although the illustrated embodiment includes four pockets associated with the front side of the shoulder harness 310 (three are visible in FIG. 30), the number of pockets may be increased or decreased, and pockets may be located on the back side (FIG. 31) of the shoulder harness.

The exemplary shoulder harness 310 is configured such that there will be a tight fit in order to insure that the charger 202a remains close to wearer generally, and in its intended location adjacent to an implanted medical device in particular. The exemplary shoulder harness 310 does not, however, include a mechanism that allows portions shoulder harness to be separated from one another when the shoulder harness is be put on and taken off. Accordingly, the exemplary shoulder harness 310 is formed from an elastomeric material, such as that sold under the trade name Neoprene, materials woven from fibers, such as those sold under the trade name Hydrofil, which include a water-absorbing component, fabrics with moisture management aspects such as those sold under the trade name Dri-Lex (e.g. Dri-Lex 1230, Dri-Lex 2000, Dri-Lex Aero Spacer and Dri-Lex Fantasia), and any combinations thereof. Such materials allow the shoulder harness to stretch and then return to its pre-stretched size and shape.

Figure 32:
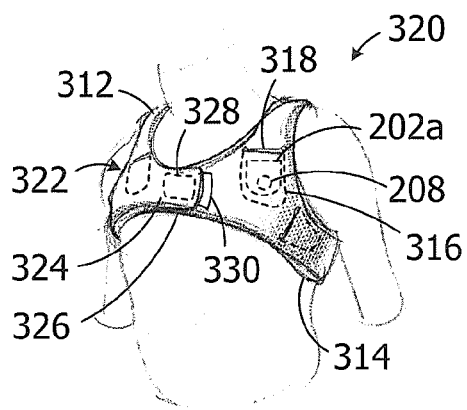
FIG. 32 is a front perspective view of a charging appliance in accordance with one embodiment of a present invention.
Figure 33:
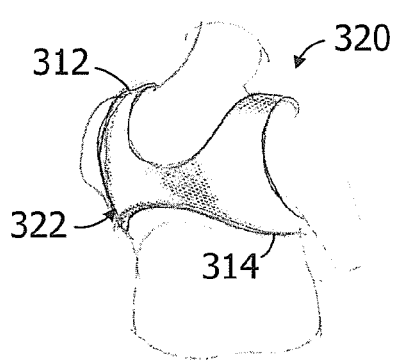
FIG. 33 is a rear perspective view of the charging appliance illustrated in FIG. 32.

Nevertheless, it should be noted that other shoulder harnesses formed form elastomeric materials may include a mechanism that allows portions shoulder harness to be separated from one another when the shoulder harness is be put on and taken off, thereby increasing the ease of use and the likelihood that a proper fit will be achieved. The charging appliance 320 illustrated in FIGS. 32 and 33 is one example of a charging appliance that includes, in addition to a charger 202a, such a shoulder harness. The exemplary shoulder harness 322 is substantially similar to shoulder harness 310 in that it includes shoulder straps 312 and chest straps 314 as well as a plurality of pockets 316 with openings 318 that are configured to receive the charger 202a. Here, however, the shoulder harness 322 is also provided with a pair of separable flaps 324 and 326 that may be releasably secured to one another with a fastener. The exemplary fastener, which consists of a length of hook (or loop) material 328 on the inner surface of flap 324 and a length of loop (or hook) material 330 on the exterior surface of flap 326, allows the size of the shoulder harness to be adjusted. Other fastening arrangements may also be employed. For example, the loop material 330 may be omitted and the exterior surface of the flap 324 formed from a hook compatible material (e.g. cotton or fleece). Other suitable fasteners include, but are not limited to, hooks, buttons, snaps, laces, and buckles.

Figure 34:
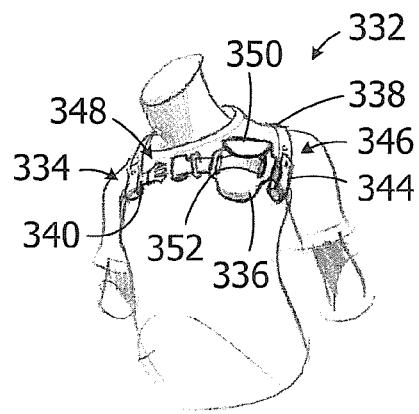
FIG. 34 is a front perspective view of a charging appliance in accordance with one embodiment of a present invention.
Figure 35:
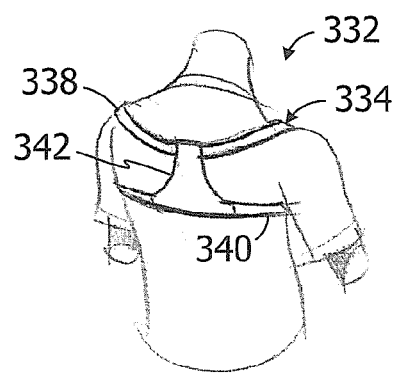
FIG. 35 is a rear perspective view of the charging appliance illustrated in FIG. 34.
Figure 36:
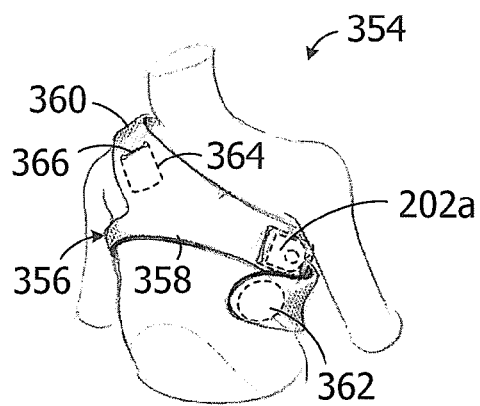
FIG. 36 is a front perspective view of a charging appliance in accordance with one embodiment of a present invention.
Figure 37:
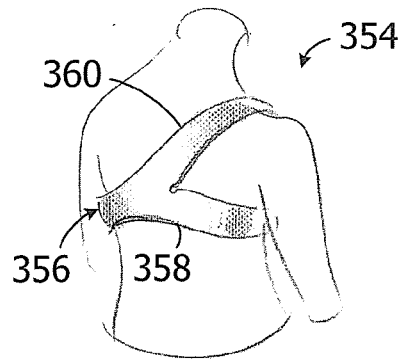
FIG. 37 is a rear perspective view of the charging appliance illustrated in FIG. 36.

Another exemplary charging appliance that includes a shoulder harness is generally represented by reference numeral 332 in FIGS. 34 and 35. The exemplary charging appliance 332 includes a shoulder harness 334, a charger 202a (not shown), and a pouch 336 with a pocket for the charger. The exemplary shoulder harness 334 consists of a shoulder strap 338, a chest strap 340, and a strap connector 342. Loops 344, though which the chest strap 340 passes, are formed in the ends of the shoulder strap 338. In the illustrated embodiment, the loops 344 are adjustable in size, thereby making the location of the chest strap 340 relative to the wearer's shoulders adjustable, through the use of a series of snap connectors 346 (as shown), a cinch buckle, or any other suitable instrumentality on the ends of the shoulder strap 338. Turning to the chest strap 340, the ends of the chest strap may be releasably secured to one another with a squeeze buckle 348 or any other suitable device. The exemplary squeeze buckle is also configured to adjust the length of the chest strap 340.

With respect to the pouch, the exemplary pouch 336 includes a flap 350 and a pair of strap slots 352. The strap slots 352 allow the pouch 336 to be carried by the shoulder strap 338 or the chest strap 340, on either side of the squeeze buckle 348, and on either side of the strap connector 342, depending on the location of the implanted medical device. The pouch 336 may also be provided with front and/or rears opening (not shown) in the manner illustrated, for example, in FIGS. 28A and 29B.

The shoulder harnesses in the exemplary appliances illustrated in FIGS. 30-35 are configured to extend over both shoulders. As illustrated for example in FIGS. 36 and 37, charging appliance 354 includes a charger 202a and a shoulder harness 356 with a chest strap 358 and a single shoulder strap 360. Both ends of the shoulder strap 360 are permanently connected to (e.g. are integral with) the chest strap 358. The chest strap 358, on the other hand, has free ends that may be wrapped around one another as the wearer puts on the harness 356. The inner surface of one of the chest strap free ends includes fastener 362 that may be used to secure the free end of the chest strap to the front surface of the chest strap 358 or shoulder strap 360. In the illustrated embodiment, the fastener 362 is a quantity of hook material and the exterior surface of the shoulder harness 356 is formed from a hook compatible material (e.g. cotton or fleece). Other suitable fasteners include, but are not limited to, hooks, buttons, snaps and buckles. Alternatively, the shoulder harness may be configured with chest strap that cannot be opened.

A plurality of pockets 364 with exterior openings 366 that are configured to receive the charger 202a are positioned on the shoulder harness 356. The pockets 364 may extend in one direction from the openings 366 (as shown) or in two directions, the number of pockets may be varied, and the pockets may be located on the back side (FIG. 37) of the shoulder harness as well as the front side.

With respect to materials, suitable materials for the shoulder harness 356 include an elastomeric material, such as that sold under the trade name Neoprene, materials woven from fibers, such as those sold under the trade name Hydrofil, which include a water-absorbing component, fabrics with moisture management aspects such as those sold under the trade name Dri-Lex (e.g. Dri-Lex 1230, Dri-Lex 2000, Dri-Lex Aero Spacer and Dri-Lex Fantasia), and any combinations thereof. Such materials are also suitable for the harnesses described below with reference to FIGS. 38-45.

Figure 38:
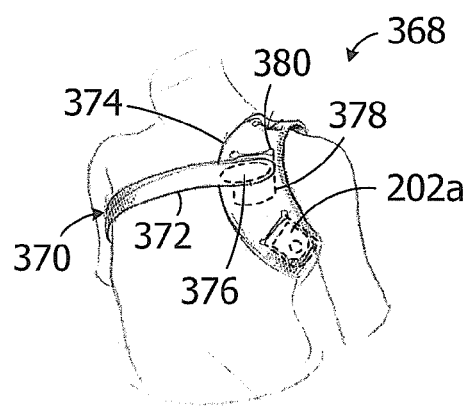
FIG. 38 is a front perspective view of a charging appliance in accordance with one embodiment of a present invention.
Figure 39:
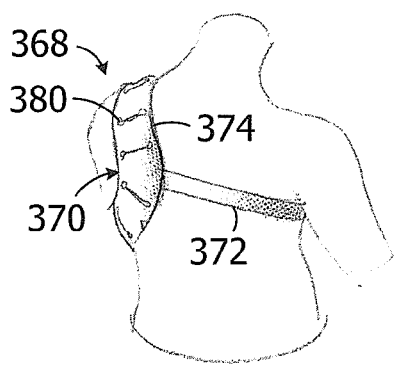
FIG. 39 is a rear perspective view of the charging appliance illustrated in FIG. 38.

Turning to FIGS. 38 and 39, the exemplary charging appliance generally represented by reference numeral 368 includes the charger 202a and a shoulder harness 370 with a chest strap 372 and a shoulder loop 374. One end of chest strap 372 is permanently secured to the back side of the shoulder loop 374 (FIG. 39), while the free end of the chest strap includes fastener 376 that may be used to secure the chest strap to the front surface of the shoulder loop 374. In the illustrated embodiment, the fastener 376 is a quantity of hook material and the exterior surface of the shoulder loop 374 is formed from a hook compatible material (e.g. cotton or fleece). Other suitable fasteners include, but are not limited to, hooks, buttons, snaps and buckles. A plurality of pockets 378 with exterior openings 380 that are configured to receive the charger 202a are positioned around the shoulder loop 374. The pockets 378 may extend in one direction from the openings 380 (as shown) or in two directions and the number of pockets may be varied.

Figure 40:
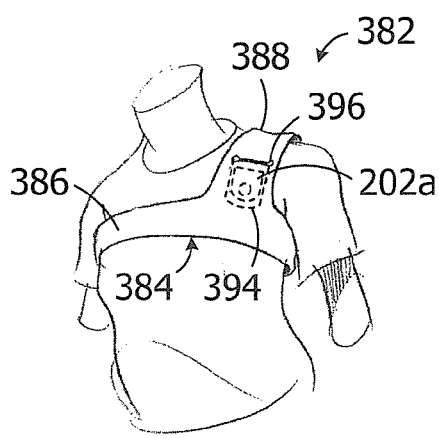
FIG. 40 is a front perspective view of a charging appliance in accordance with one embodiment of a present invention.
Figure 41:
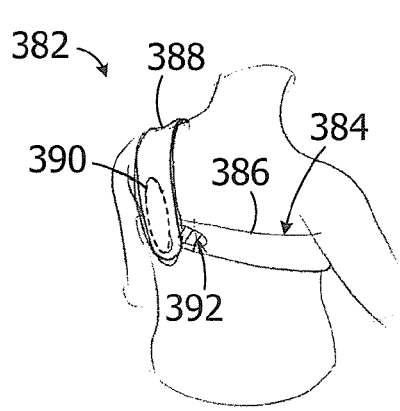
FIG. 41 is a rear perspective view of the charging appliance illustrated in FIG. 40.
Figure 47:
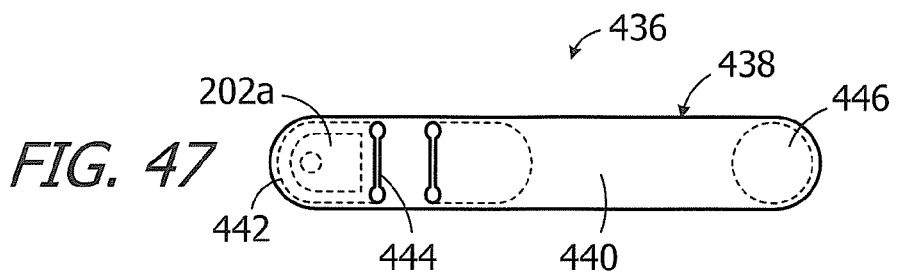
FIG. 47 is a top plan view of a charging appliance in accordance with one embodiment of a present invention.
Figure 48:
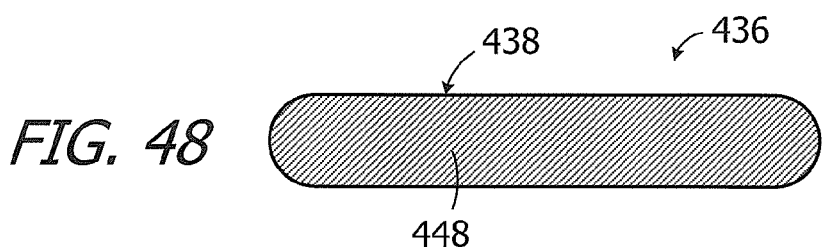
FIG. 48 is a bottom plan view of the charging appliance illustrated in FIG. 47.
Figure 49:
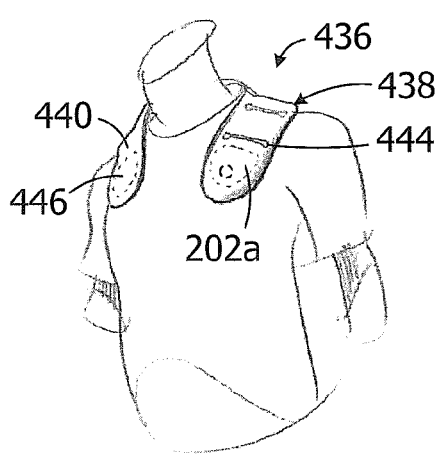
FIG. 49 is a front perspective view showing the charging appliance illustrated in FIG. 47 over both shoulders.

Another example of a charging appliance with a single shoulder strap is generally represented by reference numeral 382 in FIGS. 40 and 41. Charging appliance 382 includes the charger 202a and a shoulder harness 384 with a chest loop 386 and a shoulder strap 388. One end of the shoulder strap 388 is integral with (or otherwise permanently secured to) the front side of the chest loop 386 (FIG. 40). A fastener may be used to secure the other end of shoulder strap 388 to the rear surface of the chest loop 386 (FIG. 41). In the illustrated embodiment, the fastener consists of a length of hook (or loop) material 390 on the inner surface of shoulder strap 388 and a length of loop (or hook) material 392 on the exterior surface of chest loop 386. The configuration of the hook and loop fastener material allows the size of the shoulder strap 388 to be adjusted. Other fastening arrangements may also be employed. For example, the loop material 392 may be omitted and the exterior surface of the shoulder harness 382 may be formed from a hook compatible material (e.g. cotton or fleece). Other suitable fasteners include, but are not limited to, hooks, buttons, snaps and buckles.

A pocket 394 with an exterior opening 396 that is configured to receive the charger 202a is positioned on the shoulder strap 388. The pocket 394 may extend in one direction from the openings 396 (as shown) or in two directions, the number of pockets may be increased, one or more pockets may be located on the back side of the shoulder harness, and one or more pockets may be located on the chest ring.

Turning to FIGS. 42 and 43, the exemplary charging appliance 398 illustrated therein includes the charger 202a and a shoulder harness 400 that consists of a single shoulder strap 402 that resembles a sash. One end of the shoulder strap 402 includes a pocket 404 with an exterior opening 406 that is configured to receive the charger 202a. The location of the pocket 404, as well as the number of pockets, may be varied as desired. A fastener may be used to secure one portion of the shoulder strap 402 to another, thereby forming a loop. In the illustrated embodiment, the fastener consists of a length of hook material 408 on the inner surface of the end of the shoulder strap 402 opposite the pocket 404. The exterior surface of the shoulder strap 402 may be formed from a hook compatible material (e.g. cotton or fleece). Alternatively, a length of loop material may be secured to the exterior of the shoulder strap in the vicinity of the pocket 404. Other suitable fasteners include, but are not limited to, hooks, buttons, snaps and buckles.

An alternative single strap charging appliance is generally represented by reference numeral 410 in FIGS. 44 and 45. Here, the exemplary charging appliance includes the charger 202a and a chest harness 412 that consists of a chest strap 414 having an extension 416 for a pocket 418 with an opening 420. The pocket 418 is configured to receive the charger 202a. The exemplary chest harness 412 is configured such that there will be a tight fit in order to insure that the charger 202a remains close to wearer generally, and in its intended location adjacent to an implanted medical device in particular. The exemplary chest harness 412 does not, however, include a mechanism that allows portions chest harness to be separated from one another when the shoulder harness is be put on and taken off. Accordingly, the exemplary chest harness 412 is formed from an elastomeric material such as that sold under the trade name Neoprene.

Still another exemplary charging appliance that may be worn is generally represented by reference numeral 422 in FIG. 46. The exemplary charging appliance 422 include the charger 202a and vest 424 that is configured to mount the charger in adjacent to the implanted medical device. To that end, the inner surface of the vest 424 includes a pocket 426 with an opening (not shown) that is configured to receive the charger 202a. The vest 424 is also provided with a pair of separable flaps 428 and 430 that may be releasably secured to one another with a fastener. The exemplary fastener, which consists of a length of hook (or loop) material 432 on the inner surface of flap 428 and a length of loop (or hook) material 434 on the exterior surface of flap 430, allows the wearer to easily put on, remove, and adjust the size of the vest 424. Other fastening arrangements may also be employed. For example, the loop material 434 may be omitted and the exterior surface of the flap 430 may be formed from a hook compatible material (e.g. cotton or fleece). Other suitable fasteners include, but are not limited to, hooks, buttons, snaps, laces, zippers and buckles.

It should also be noted here that although the illustrated embodiment includes a single pocket 426 that is associated with the front side of the vest 424 near the upper chest. Other embodiments may include pockets at other location on the vest 424 or other garment (e.g. a coat, apron or pull-over vest), multiple pockets, and one or more pockets on the exterior of the vest or other garment.

Figure 50:
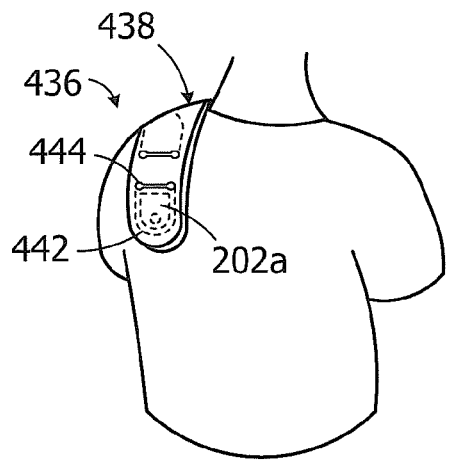
FIG. 50 is a rear perspective view showing the charging appliance illustrated in FIG. 47 over a single shoulder.

Other exemplary charging appliances are configured to extend partially or completely around the wearer's neck. One such appliance, which is generally represented by reference numeral 436 in FIGS. 47-50, includes the charger 202a and a shoulder drape 438 that is configured to carry the charger and to extend partially around the wearer's neck. More specifically, the shoulder drape 438 may be positioned over both shoulders and behind the neck (FIG. 49), over both shoulders and in front of the neck, or over a single shoulder and next to the neck (FIG. 50). The exemplary shoulder drape 438 includes a top portion 440 with a pair of pockets 442 having openings 444 that are configured to receive the charger 202a. Although the shoulder drape 438 in the illustrated embodiment has a generally linear overall shape, other shoulder drapes may have a curved overall shape.

The shoulder drape 438 may also provided with structures that reduce the likelihood that the charging appliance 436 will move relative to the user once charger 202a has been positioned adjacent to the implanted medical device. More specifically, in the illustrated embodiment, the shoulder drape 438 includes a permanent counterweight 446 on the end opposite the pockets 442 and/or a slip resistant bottom surface 448 (e.g. a rubber or textured surface). Suitable materials for the top portion 440 include, but are not limited to, fleece, microsuede, cloth, fabrics with moisture management aspects such as those sold under the trade name Dri-Lex (e.g. Dri-Lex Aero Spacer) or other materials that are soft, comfortable, and durable. In other embodiments, the permanent counterweight may be replaced by a charger pocket with an opening. The charger pocket may be occupied by a second charger in those instances where wearer has implanted medical devices on both sides of his/her chest, or by a removable counterweight.

Figure 51:
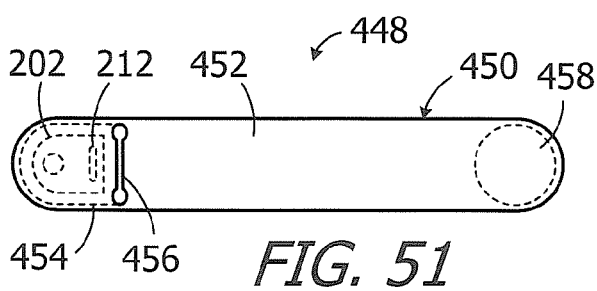
FIG. 51 is a top plan view of a charging appliance in accordance with one embodiment of a present invention.
Figure 52:
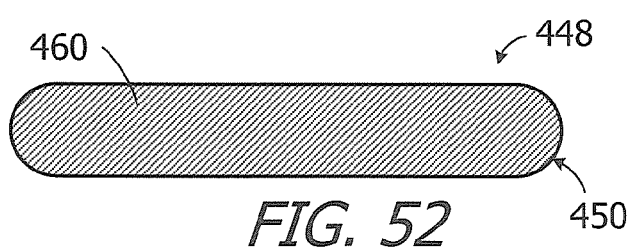
FIG. 52 is a bottom plan view of the charging appliance illustrated in FIG. 51.
Figure 53:
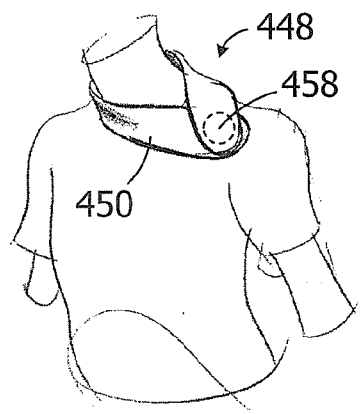
FIG. 53 is a front perspective view showing the charging appliance illustrated in FIG. 51 being worn.

Another exemplary charging appliance that is configured to be positioned around the neck is generally represented by reference numeral 448 is FIGS. 51-53. Here, however, the charging appliance is configured such that the ends of the shoulder drape may be releasably secured to one another. More specifically, the exemplary charging appliance 448 includes the charger 202 (with magnet 212), a shoulder drape 450 with a top portion 452 that has a pocket 454 and an opening 456 which is configured to receive the charger, and a magnet 458 that is attracted to the magnet 212. The shoulder drape 450 may also be provided with a slip resistant bottom surface 460 (e.g. a rubber or textured surface) in order to reduce the likelihood that the charging appliance 448 will move relative to the user once shoulder drape 450 has been positioned in, for example, the manner illustrated in FIG. 53 with the charger adjacent to the implanted medical device.

As alluded to above, the fastening arrangement employed by the exemplary charging appliance 448 includes the magnets 212 and 458. A variety of other fastening arrangements may be employed to secure the ends of the shoulder drape to one another. By way of example, the charger 202a, which does not include the additional magnet 212, may be employed. Here, the magnet 458 would cooperate with either the inductor magnet, or an additional magnet added to the shoulder drape 450 adjacent to the pocket 454. Other alternatives include, but are not limited to, snaps, buttons, and hook and loop fasteners.

Figure 54:
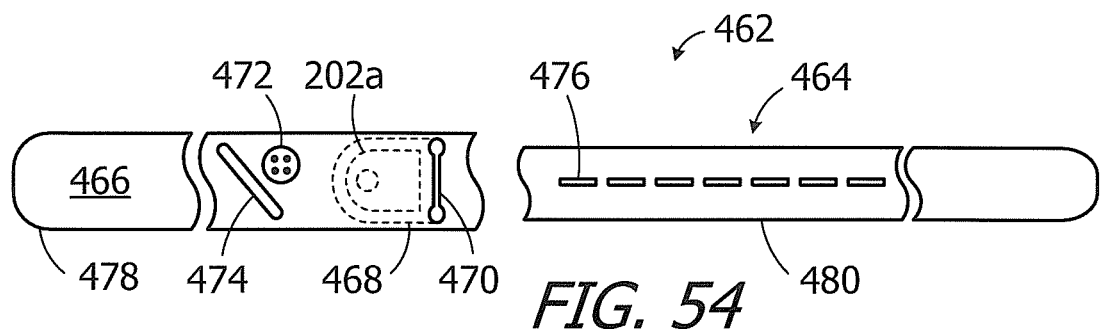
FIG. 54 is a top plan view of a charging appliance in accordance with one embodiment of a present invention.
Figure 55:
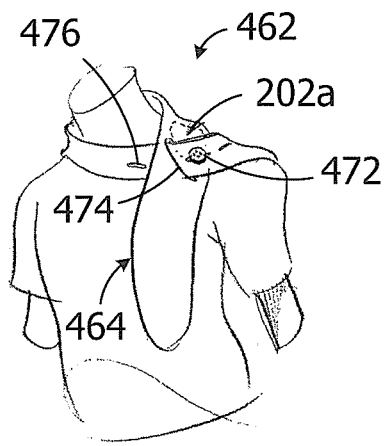
FIG. 55 is a front perspective view showing the charging appliance illustrated in FIG. 54 being worn.
Figure 56:
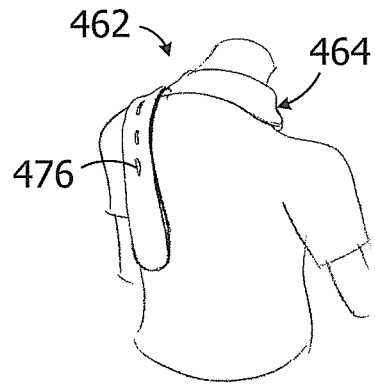
FIG. 56 is a rear perspective view showing the charging appliance illustrated in FIG. 54 being worn.

Turning to FIGS. 54-58, the exemplary embodiments also include a wide variety of scarf-like charging appliances. Referring first to FIGS. 54-56, the exemplary charging appliance 462 includes the charger 202a and a scarf 464 that is configured to mount the charger adjacent to the implanted medical device. The exemplary scarf 464 consists of an elongate flexible body 466, which has a pocket 468 with an opening 470 that is configured to receive the charger 202a, and a fastening arrangement that maintains the scarf 464 in the desired orientation. In the illustrated embodiment, the fastening arrangement includes a button 472, a slot 474 and a plurality of button holes 476. The portion of the flexible body 466 with the button holes 476 may be inserted through the slot 474 and the button 472 secured to the desired button hole, as is illustrated in FIG. 55. To that end, the elongate flexible body has a relative wide portion 478, with which the pocket 468, button 472 and slot 474 are associated, and a relatively narrow portion 480 with which the button holes 476 are associated. Alternatively, the slot 474 may be omitted and the width of the elongate flexible body uniform from one end to another.

Figure 57:
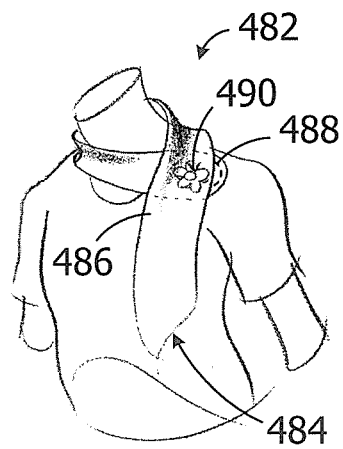
FIG. 57 is a front perspective view of a charging appliance in accordance with one embodiment of a present invention.

Another exemplary scarf-like charging appliance, which is generally represented by reference numeral 482 in FIG. 57, includes the charger 202 (not shown), a scarf 484 consisting of an elongate flexible body 486 with a pocket 488 having an opening that is configured to receive the charger, and a fastening arrangement that maintains the scarf 482 in the desired orientation. Here, the fastening arrangement consists of the charger magnet 212 (or the inductor magnet) and a magnet 490, such as the exemplary decorative magnet, which is attracted to the magnet 212 and is not an integral part of the elongate flexible body 486. After the elongate flexible body 486 has been positioned such that the charger is aligned with the implanted medical device, the magnet 490 may be secured to the magnet 212 (or inductor magnet) to hold the charging appliance 482 in place. In other embodiments, the magnetic fastening arrangement may be replaced with a mechanical fastener such as a clip or a button.

Figure 58:
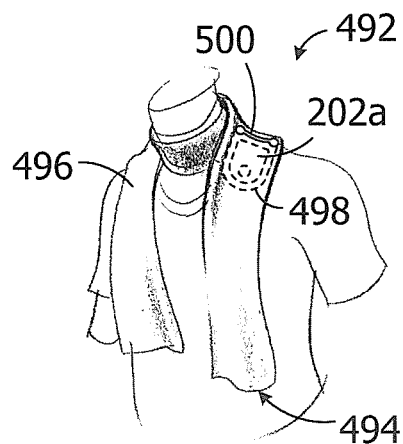
FIG. 58 is a front perspective view of a charging appliance in accordance with one embodiment of a present invention.

Turning to FIG. 58, the exemplary scarf-like charging appliance 492 illustrated therein includes a charger 202a and a scarf 494 that is configured to mount the charger in adjacent to the implanted medical device. The exemplary scarf 494 consists of an elongate flexible body 496, which has a pocket 498 with an opening 500 that is configured to receive the charger 202a. Here, there is no fastening arrangement and the appliance 492 may be held in place by simply wrapping the scarf 494 around the neck as shown.

With respect to materials, suitable materials for the scarves 464, 484 and 494 include, but are not limited to, fleece, cotton, silk, Neoprene, polyester, and fabrics with moisture management aspects such as those sold under the trade name Dri-Lex (e.g. Dri-Lex 1230, Dri-Lex 2000 and Dri-Lex Fantasia). It should also be noted here that the scarves may be configured to place charger against higher on the neck than is shown in the Figures.

Figure 59:
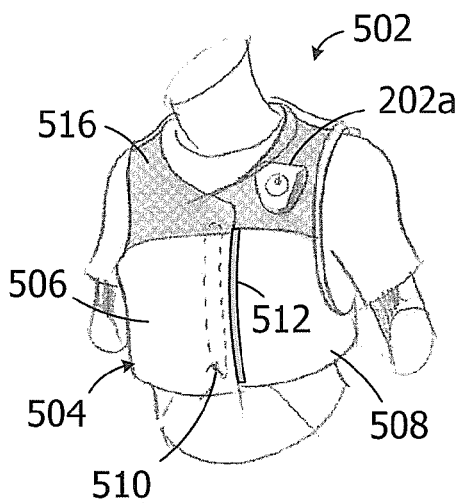
FIG. 59 is a front perspective view of a charging appliance in accordance with one embodiment of a present invention.
Figure 60:
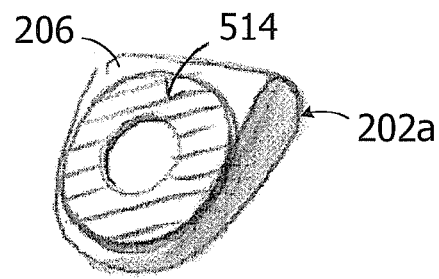
FIG. 60 is a rear perspective view of a portion of the charging appliance illustrated in FIG. 59.
Figure 61:
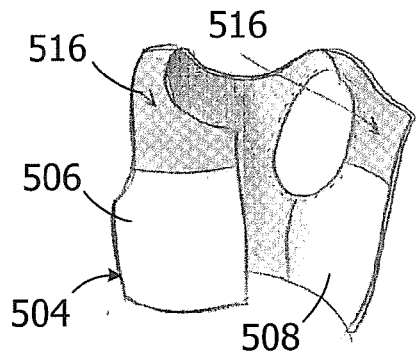
FIG. 61 is front view of a garment in accordance with one embodiment of a present invention.
Figure 62:
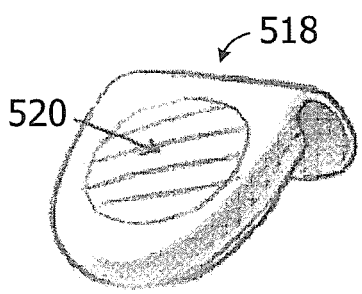
FIG. 62 is a rear perspective view of a charger pouch in accordance with one embodiment of a present invention.
Figure 63:
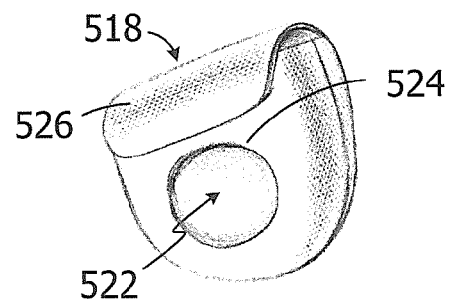
FIG. 63 is a front perspective view of the charger pouch illustrated in FIG. 62.

Chargers, charger mounting apparatus, and/or charging appliances may also be configured so as to allow the charger to be precisely and removably positioned in a variety of locations relative to the user's body. Referring first to FIGS. 59 and 60, the exemplary charging appliance 502 includes the charger 202a, garment 504, and a mounting arrangement that is configured to mount the charger on the garment adjacent to the implanted medical device. In the illustrated embodiment, the garment 504 is a vest with flaps 506 and 508 and fasteners, such as a length of hook material 510 on the inner surface of one flap and a length of loop material 512 on the exterior surface of the other. The length of loop material 512 is wider than the length of hook material 510 in order to accommodate wearers of different size. Other fastening arrangements may also be employed. For example, the loop material 512 may be omitted and the exterior surface of the flap 508 may be formed from a hook compatible material (e.g. cotton or fleece). Other suitable fasteners include, but are not limited to, hooks, buttons, snaps, zippers and buckles. Moreover, in other implementations, a pullover type vest without openable flaps and fasteners may be employed.

Turning to the manner in which the charger is mounted on the garment in the exemplary charging appliance 502 illustrated in FIGS. 59 and 60, the charger 202a and the garment 504 are provided with respective areas of hook material 514 and loop material 516. The garment 504 may be formed from any suitable garment-type material as well as from fabrics with moisture management aspects such as those sold under the trade name Dri-Lex (e.g. Dri-Lex 2000 and Dri-Lex Fantasia). Although the hook material 514 is positioned on the rear of the charger housing 206 in the illustrated embodiment, it may also be positioned on the front of the charger housing. The loop material 516 is located on the front shoulder and upper chest portion of the exterior each flap 506 and 508. The portions of the flaps 506 and 508 covered with (or formed by) the loop material 516 may be increased or decreased, and all or part of the back side of the garment may be covered with (or formed by) the loop material. Additionally, or alternatively, some or all of the inner surfaces of the garment may be covered with (or formed by) the loop material, as is the case of the exemplary garment 504a illustrated in FIG. 61. Material such as cotton, fleece, unbroken loop Neoprene or other hook compatible material may also be substituted for the hook compatible loop material 516.

Another alternative is to employ a pouch that is configured to carry a charger and a mounting apparatus that is configured to secure to the pouch to the garment. One such pouch is the exemplary pouch 518 illustrated in FIGS. 62 and 63, which may mounted on a garment by way of loop material or other hook compatible material on a garment (e.g. loop material 516 on garment 504) and an area of hook material 520 on the pouch. With respect to the particular configuration of the pouch, the exemplary pouch 518 include a pocket 522 for the charger 202a, a front aperture 524, and a flap 526. Other exemplary pouch configurations include, but are not limited to, those described above with reference to FIGS. 29A-29E.

It should also be noted that garments with hook material that functions in the manner illustrated in FIG. 59 are not limited to vests. Shirts, pants, and undergarments are other examples of garments which may include (or be at least partially formed by) loop or other fastener material in order to facilitate the mounting of a charger or charger pouch that includes corresponding hook or other fastener material. Moreover, the above-described shoulder and chest harnesses (FIGS. 30-45), shoulder drapes (FIGS. 47-50) and neck-related apparatus (FIGS. 51-58) may be reconfigured such that the charger pockets are eliminated and regions of these devices include, or are formed by, loop material or other hook compatible material to which the hook material on the charger illustrated in FIG. 60 and/or pouch illustrated in FIGS. 62 and 63 can be secured.

In other implementations, one or more inductors may be permanently secured to or within a wearable device, such as any of the wearable devices illustrated in or described in the context of FIGS. 3-17, 19 and 30-59, to form a charging appliance that includes the wearable device. For example, in the exemplary charging appliance 528 illustrated in FIGS. 64-66, an inductor apparatus 530 carries an inductor and inductor related circuitry (e.g. inductor 24c and inductor related circuitry 25) and is permanently secured to the inner surface of the above-described knee brace 180. The inductor 24c and inductor related circuitry 25 may be molded into an epoxy, silicone, or urethane structure that is carried within a plastic case 532. Alternatively, the inductor 24c and inductor related circuitry 25 may be carried within a polycarbonate case, that is itself coated with an insulating encapsulate such as silicone, rubber-like polymers, Teflon, and other plastics. In either embodiment, the inductor apparatus 530 will be electrically insulated from the wearer and water resistant. Suitable devices for securing the inductor apparatus 530 to the cuff 182 or other portion of the knee brace 180 include adhesives and/or mechanical fasteners that are configured not to be released after they have been fastened.

Figure 64:
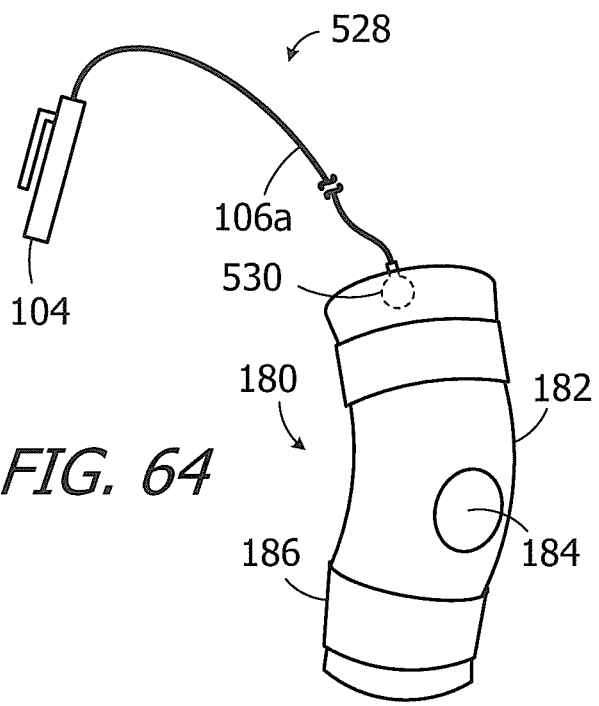
FIG. 64 is a perspective view of a charging appliance in accordance with one embodiment of a present invention.
Figure 65:
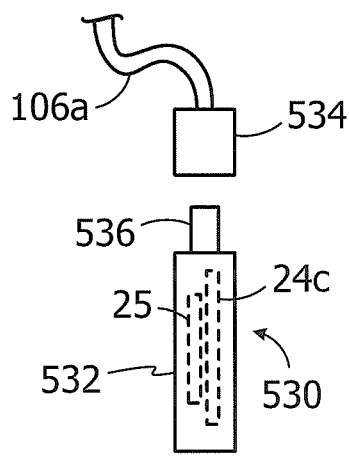
FIG. 65 is a side view of a portion of the charging appliance illustrated in FIG. 64.
Figure 66:
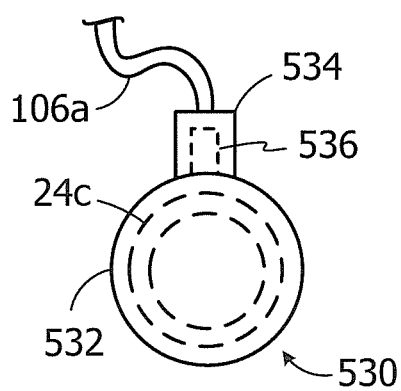
FIG. 66 is a plan view of a portion of the charging appliance illustrated in FIG. 64.
Figure 81:
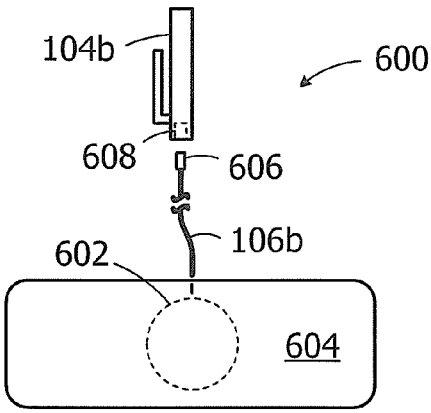
FIG. 81 is a plan view of a charging appliance in accordance with one embodiment of a present invention.

The exemplary embodiment illustrated in FIGS. 64-66 includes a cable 106a with a connector 534 that is configured to mate with a corresponding connector 536. So configured, the cable 106a may be used to connect the power supply and control apparatus within remote housing 104 to, or disconnect the power supply and control apparatus from, the inductor 24c and inductor related circuitry 25 in the inductor apparatus 530. In the embodiment illustrated in FIGS. 64-66, the cable 106a is permanently secured to the housing 104. However, in other embodiments, the cable 106a may be permanently secured to the inductor apparatus and the connector 534 used to connect the cable to the remote housing. Another alternative is to provide a cable with connectors at both ends.

Ear muffs are another example of a wearable device which may form part of a charging appliance and, to that end, the exemplary charging appliance 538 illustrated in FIGS. 67 and 68 includes the inductor apparatus 530 and ear muffs 540. The ear muffs 540 consist of a pair of ear pads 542 and a resilient head band 544 on which the ear pads are mounted. The inductor apparatus 530 is carried within one of the ear pads 542 and, to that end, the ear pad includes an aperture 546 to facilitate mating of the connectors 534 and 536. The power supply and control apparatus within the remote housing 104 may, therefore, be connected to and disconnected from the inductor apparatus 530 as desired.

Other exemplary charging appliances that include the remote housing 104, as well as the power supply and control apparatus therein, the inductor apparatus 530, and a wearable device are illustrated in FIGS. 69-80. Although the remote housing 104 and the power supply and control apparatus therein are not shown in FIGS. 69-80, the remote housing and power supply and control apparatus are part of the exemplary charging appliances as is indicated by the presence of the cable 106a and connector 534.

Turning first to FIG. 69, in the exemplary charging appliance 548, the inductor apparatus 530 is secured to the inner surface of a belt buckle 550. The charging appliance 552 illustrated in FIG. 70 includes an inductor apparatus 530 that is carried within an eyeglass retainer strap 554. As such, the inductor within the inductor apparatus will be positioned behind the wearer's neck. Prosthetic hair may also form part of a charging appliance. The charging appliance 556 illustrated in FIG. 71, for example, includes a an inductor apparatus 530 that is secured to a wig 558.

Jewelry and other decorative accessories are other examples of the types of wearable devices that may be incorporated, along with an inductor apparatus 530 or similar device, into a charging appliance. For example, the charging appliance 560 illustrated in FIG. 72 includes an inductor apparatus 530 that is secured to the hair clip portion 562 of a barrette 563.

Turning to FIGS. 73-76, other decorative charging appliances are configured to position an inductor at any desired location around the wearer's neck. The charging appliance 564 illustrated in FIG. 73, for example, includes a dog collar type neck accessory 566 and the inductor apparatus 530. The inductor apparatus 530 is connected to the remote housing 104 (not shown) and the power supply and control apparatus therein by the cable 106a and connectors 534 and 536. In the illustrated embodiment, the neck accessory consists of a leather strip 568 with a connector (not shown) and a plurality of metal studs 570. The inductor apparatus 530 may be glued or otherwise secured to the inner surface of the leather strip 568 (as shown) or held between the plies of a multi-ply structure.

In another charging appliance, which is generally represented by reference numeral 572 in FIG. 74, the inductor apparatus 530 is secured to neck ribbon 574. Here too, the inductor apparatus 530 is connected to the remote housing and the power supply and control apparatus therein by the cable 106a and connectors 534 and 536.

Turning to FIGS. 75 and 76, the exemplary charging appliance 576 includes a necklace 578 with a plurality of decorative discs 580. The inductor apparatus 530 is carried within one of the decorative discs 580. An aperture 582 is provided in order to allow the connectors 534 and 536 and, therefore, the power supply and control apparatus and the inductor, to be connected to one another. The necklace 578 may be the illustrated choker length, or longer, depending on the location of the implanted medical device.

In the exemplary charging appliance 584 illustrated in FIGS. 77 and 78, the inductor apparatus 530 is carried within an earring 586 that has an ear clip 588 and an aperture 590. Here too, the aperture allows the connectors 534 and 536 and, therefore, the power supply and control apparatus and the inductor, to be connected to one another.

Other types of jewelry to which an inductor apparatus may be secured include, but are not limited to piercings, wrist watches, headbands, bandanas, anklets, bracelets, pendants, and broaces.

As alluded to above in the context of the knee brace illustrated in FIGS. 64-66, an externally worn medical device is another example of a device that may be part of a charging appliance. Other exemplary charging appliances that include externally worn medical device are illustrated in FIGS. 79 and 80. Referring first to FIG. 79, the charging appliance 592 includes a thyroid guard 594 and the inductor apparatus 530. The inductor apparatus 530 may be secured to the neck portion of the thyroid guard (as shown) or to the portion that hangs downwardly from the neck portion. The remote housing and the power supply and control apparatus therein may be connected to the inductor apparatus 530 by the cable 106a. Turning to FIG. 80, the exemplary charging appliance 596 includes a neck brace 598 with the inductor apparatus 530 secured thereto. The remote housing and the power supply and control apparatus therein may be connected to the inductor apparatus 530 by the cable 106a. The inductor apparatus 530 may be glued or otherwise secured to the inner surface of the thyroid guard or neck brace (as shown), one the outer surface, or carried between the inner and outer surfaces.

Still other charging appliances include an inductor apparatus and a mounting device that is configured to adhere to the wearer's skin. Such mounting devices permit the an inductor to be positioned at essentially any location on the wearer's body. For example, the charging appliance 600 illustrated in FIGS. 81 and 82 includes an inductor apparatus 602 with an inductor and inductor related circuitry (e.g. inductor 24c and inductor related circuitry 25), an adhesive strip 604, and a remote housing 104b, with the above-described power supply and control apparatus and user interface. The remote housing 104b may be connected to the inductor apparatus 602 in the manner described below.

The inductor and inductor related circuitry in the exemplary inductor apparatus 602 may be molded into an epoxy, silicone, or urethane structure that is carried within a plastic case. Alternatively, the inductor and inductor related circuitry may be carried within a polycarbonate case, that is itself coated with an insulating encapsulate such as silicone, rubber-like polymers, Teflon, and other plastics. In either embodiment, the inductor apparatus 602 will be electrically insulated from the wearer and water resistant. The inductor apparatus 602 is also provided with a cable 106b that has a connector 606. The connector 606 is configured to mate with a corresponding connector 608 on the remote housing 104b. In the exemplary embodiment, the cable 106b is permanently secured to the inductor apparatus 602. However, in other embodiments, the cable 106a may be permanently secured to the remote housing and a connector used to connect the cable to the inductor apparatus. Another alternative is to provide a cable with connectors at both ends.

Figure 82:
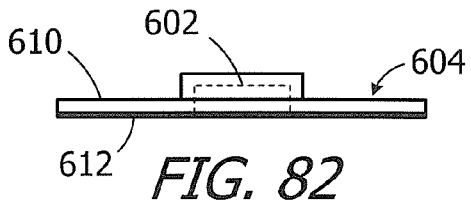
FIG. 82 is a side view of a portion of the charging appliance illustrated in FIG. 81.
Figure 83:
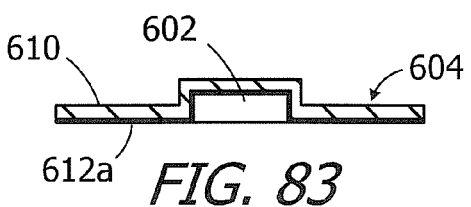
FIG. 83 is a side, partial section view of an alternate portion of the charging appliance illustrated in FIG. 81.

The exemplary adhesive strip 604, which is similar to those commonly associated with conventional adhesive bandages, includes a backing 610 and a layer of adhesive 612. Suitable materials for the backing 610 include, but are not limited to, woven fabrics, plastics, and latex rubbers, while the adhesive may be a hypoallergenic adhesive that will adhere to the skin, yet exhibit enough release when intentionally removed so as not to tear the skin or leave a residue. The backing 610 may be pressed over the inductor apparatus 602 prior to the application of the adhesive so that the adhesive layer 612 covers the inductor apparatus as well as the backing, as shown in FIG. 82. Alternatively, as illustrated for example in FIG. 83, the adhesive layer 612a may be applied to the backing 610 prior to the backing being pressed over the inductor apparatus 602. In either case, a release liner (not shown) may be placed over adhesive layer 612 (or 612a) to facilitate storage.

Figure 84:
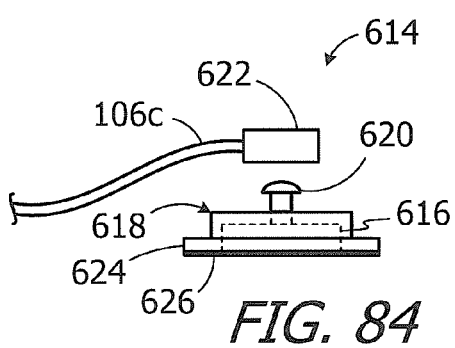
FIG. 84 is a side view of a charging appliance in accordance with one embodiment of a present invention.
Figure 85:
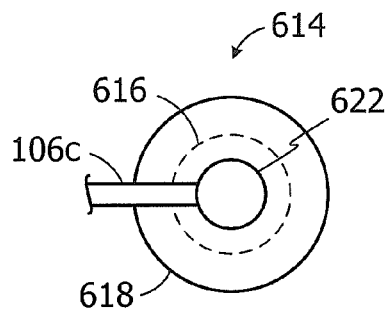
FIG. 85 is a plan view of a portion of the charging appliance illustrated in FIG. 84.

Another charging appliance that is configured to adhere to the wearer's skin is generally represented by reference numeral 614 in FIGS. 84 and 85. Charging appliance 614 includes an inductor apparatus 616 with an inductor and inductor related circuitry (e.g. inductor 24c and inductor related circuitry 25), an adhesive disk 618, and a remote housing 104, with the above-described power supply and control apparatus and user interface. The remote housing 104 may be connected to the inductor apparatus 616 in the manner described below.

The inductor and inductor related circuitry in the exemplary inductor apparatus 616 may be molded into an epoxy, silicone, or urethane structure that is carried within a plastic case. Alternatively, the inductor and inductor related circuitry may be carried within a polycarbonate case, that is itself coated with an insulating encapsulate such as silicone, rubber-like polymers, Teflon, and other plastics. In either embodiment, the inductor apparatus 616 will be electrically insulated from the wearer and water resistant. The inductor apparatus 616 is also provided with a connector 620 that extends through the adhesive disk 618. Suitable connectors include the types frequently found on conventional EKG electrodes. A cable 106c, with a corresponding connector 622, may be used to connect the power supply and control apparatus within the remote housing 104 to, or disconnect the power supply and control apparatus from, the inductor and inductor related circuitry in the inductor apparatus 616. However, in other embodiments, the cable may be permanently secured to the inductor apparatus and a connector used to connect the cable to the remote housing. Another alternative is to provide a cable with connectors at both ends.

The exemplary adhesive disk 618, which is similar to those commonly associated with conventional EKG electrodes, includes a backing 624 and a layer of adhesive 626. Suitable materials for the backing 624 include, but are not limited to, woven fabrics, plastics, and latex rubbers, while the adhesive 626 may be a hypoallergenic adhesive that will adhere to the skin, yet exhibit enough release when intentionally removed so as not to tear the skin or leave a residue. The backing 624 may be pressed over the inductor apparatus 616 prior to the application of the adhesive so that the adhesive layer 626 covers the inductor apparatus as well as the backing (as shown). Alternatively, an adhesive layer may be applied to the backing 624 prior to the backing being pressed over the inductor apparatus 602. In either case, a release liner (not shown) may be placed over the adhesive layer to facilitate storage.

Figure 86:
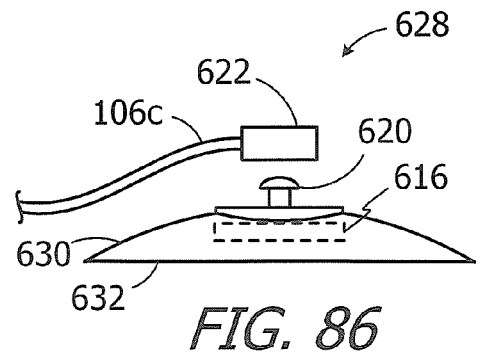
FIG. 86 is a side view of a charging appliance in accordance with one embodiment of a present invention in a relaxed state.
Figure 87:
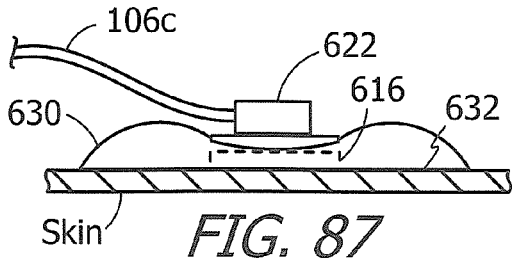
FIG. 87 is a side view of the charging appliance illustrated in FIG. 86 secured to skin.
Figure 95:
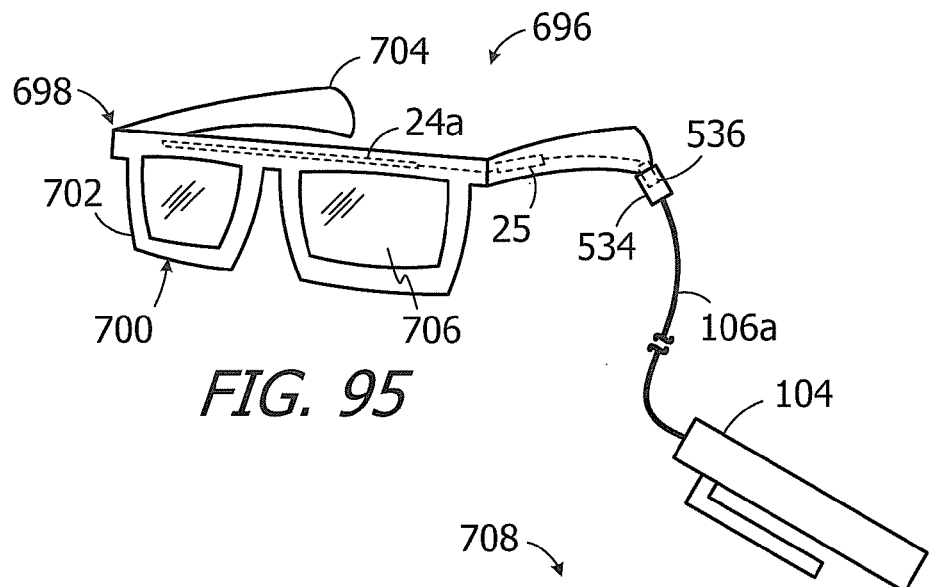
FIG. 95 is a perspective view of a charging appliance in accordance with one embodiment of a present invention.

The exemplary charging appliance 628 illustrated in FIGS. 86 and 87 is also configured to adhere to the wearer's skin and, to that end, includes a suction cup 630 in addition to the inductor apparatus 616 and remote housing 104. The inductor apparatus 616, which is secured to the inner surface of the suction cup (e.g. with adhesive), is connected to the power supply and control apparatus associated with the remote housing 104 by the cable 106c. To that end, the connector 620 extends through an otherwise sealed aperture (not shown) in the top portion of the suction cup 630 such that it may be connected to the connector 622 on cable 106c.

Although the charging appliance is not limited to any particular suction cup, the exemplary suction cup 630 is circular in shape when viewed in plan, has a smooth circular sealing surface 632, and is formed from a flexible material such as rubber, PVC plastic or neoprene. The suction cup 630 is biased to the relaxed state illustrated in FIG. 86. When the suction cup 630 is pressed against the wearer's skin, air is forced out of the interior of the suction cup, a seal is created between the sealing surface 632 and the skin, and the vacuum created by the biasing force of the suction cup secures the cup to the skin, as is shown in FIG. 87. The respective sizes and shapes the inductor apparatus 616 and suction cup 630 result in the inductor apparatus being in close proximity to, or in contact with, the skin.

Other charging appliances include an inductor that extends around a portion of the body. One such charging appliance is generally represented by reference numeral 634 in FIGS. 88 and 89. The charging appliance 634 includes an inductor apparatus 636 and a remote housing 104, with the above-described power supply and control apparatus and user interface.

The exemplary inductor apparatus 636, which is configured to look like a loop necklace, includes an inductor portion 638 and a clasp 640. The inductor portion 638 consists of an inductor coil 642 and an electrically insulating exterior portion 644 (FIG. 90). The exemplary clasp 640, which physically connects the free ends of the inductor portion 638, includes a first portion 646, a second portion 648 and a latch 650 that releasably secures the first and second portions to one another. The inductor related circuitry 25 is molded into the first clasp portion 646. A conductor line 652, which includes separable sections in the first and second clasp portions 646 and 648, electrically connects the free ends of the inductor coil 642 to the circuitry 25 when the clasp 640 is closed (as shown). The clasp 640 also includes a connector 654 that is configured to mate with a connector 656 on the cable 106d, thereby connecting the inductor apparatus 636 to the power supply and control apparatus within the remote housing 104. In other embodiments, the cable 106d may be permanently secured to the clasp 640 and a connector used to connect the cable to the remote housing, or a cable with connectors at both ends may be provided. In still other embodiments, where the loop formed by the inductor portion 638 is large enough to fit over the wearer's head, the clasp 640 may be replaced by an unopenable structure that otherwise performs the same functions as the clasp.

In the illustrated embodiment, the inductor apparatus 636 is a resilient structure and may be removed from the wearer's neck by unlatching the clasp 640, thereby allowing the first and second clasp portions 646 and 648 to be separated from one another, and pulling the free ends of the inductor portion 638 away from one another. To that end, suitable materials for the inductor coil 642 include, but are not limited to, copper, copper alloys, and silver, and suitable materials for the electrically insulating exterior portion 644 include, but are not limited to, plastics such as PVC that is the desired color or is painted the desired color. Suitable materials for the clasp 640 include, but are not limited to, plastics such as PVC. Alternatively, the exterior portion 644 may be partially covered by a decorative element formed from gold or other suitable metals and non-metals, as is described below with reference to FIG. 93. The configuration of clasp 640 and exterior portion 644 should also be such that the charging appliance is waterproof (or at least water resistant).

It should also be noted that, although inductor coil 642 is in the form of a singe loop in the illustrated embodiment, other embodiments may include a plurality of loops within the electrically insulating exterior portion 644 and a connector similar to that described below with reference to FIG. 91.

Another charging appliance which includes an inductor that extends around the associated portion of the body is generally represented by reference numeral 658 in FIGS. 91 and 92. The charging appliance 634 includes an inductor apparatus 660 and a remote housing 104, with the above-described power supply and control apparatus and user interface. The remote housing 104 may be connected to the inductor apparatus 660 in the manner described below.

The exemplary inductor apparatus 660, which is configured to look like a multiple ring necklace, includes a plurality of rings 662*a-d*, a clasp 664, and an inductor coil 666 that passes through the rings and clasp. The clasp 664 has first and second portions 668 and 670 and a latch 672. Each of the rings 662*a-d* has a pair of free ends that are in close proximity to one another and respectively secured to the clasp portions 668 and 670. The clasp 664 is also provided with a connector 674 that is configured to mate with a connector 656 on a cable 106*e*, thereby connecting the inductor apparatus 660 to the power supply and control apparatus within the remote housing 104. The cable 106*e* also includes a housing 675 that carries the inductor related circuitry 25. In other embodiments, the cable 106*e* may be permanently secured to the clasp 664 and a connector used to connect the cable to the remote housing, or a cable with connectors at both ends may be provided. Also, the inductor related circuitry 25 may be carried within the clasp 664 and the housing 275 may be omitted.

The illustrated inductor coil 666 includes a first free end that is associated with one of the free ends of ring 662*a* and is connected to the connector 674. The inductor coil 666 also extends through ring 662*a* to the other free end thereof, though the clasp 664 to one of the free ends of ring 662*b*, through ring 662*b* to the other free end thereof, though the clasp to one of the free ends of ring 662*c*, through ring 662*c* to the other free end thereof, though the clasp to one of the free ends of ring 662*d*, and through ring 662*d* to the other free end thereof. The free end of the inductor coil 666 associated with ring 666*d* is connected to the connector 674. In order to accommodate passage through the separable clasp 664, the inductor coil 666 has three discontinuities. The portions of the inductor coil 666 on opposite sides of each discontinuity are connected to one another when the clasp 664 is closed, and disconnected when the clasp is open.

Turning to FIG. 93, the exemplary rings 662*a-d* include an insulating main portion 676, though which the inductor coil 666 passes, and a decorative portion 678 that is on the exterior side of the main portion that will be visible when the inductor apparatus 660 is worn. The inductor apparatus 660 is also resilient so that it can be spread apart when being put on and taken off. As such, suitable materials for the inductor coil 666 include, but are not limited to, metals such as copper, copper alloys, and silver, suitable materials for the main portion 676 include, but are not limited to, plastics such as PVC, and suitable materials for the decorative portion 678 include, but are not limited to gold, silver, other metals and decorative non-metals. Also, the configuration of clasp 664 and main portion 676 should also be such that the charging appliance is waterproof (or at least water resistant).

In one alternative implementation, the rings 662*a-d* may be formed by a flexible, continuous coil-like structure that forms a plurality of loops and can be stretched to fit over the wearer's head. Here, the clasp will simply connect the free ends of the inductor coil within the coil-like structure to a connector (e.g. the connector 674). In other alternative implementations, which may include multiple rings or a single coil-like structure, the decorative portion may be omitted and the main portion 676 formed from a plastic that is (or is painted) the desired color.

The exemplary charging appliance 680 illustrated in FIG. 94, which also includes an inductor that extends around the associated portion of the body, includes an inductor apparatus 682 and a remote housing 104, with the above-described power supply and control apparatus and user interface. The exemplary inductor apparatus 682 is also configured to look like a necklace and includes a flexible band 684, a clasp 686, and an inductor coil 688 embedded within the flexible band. The inductor related circuitry 25 and a connector 654, which mates with the connector 656 on cable 106*d* to connect the inductor apparatus 682 to the power supply and control apparatus within the remote housing 104, are also embedded within the flexible band 684. In other embodiments, the cable 106*d* may be permanently secured to the free ends of the coil 688 a connector used to connect the cable to the remote housing. Another alternative is to provide a cable with connectors at both ends.

In the illustrated embodiment, the clasp 686 has first and second portions 690 and 692 and a latch 694. The inductor coil 688 passes through the clasp 686 and, to that end, has a pair discontinuities. The portions of the inductor coil 688 on opposite sides of each discontinuity are connected to one another when the clasp 686 is closed, and disconnected when the clasp is open.

With respect to materials, suitable materials for the flexible band include, but are not limited to, rubber, silicone and fabric (with insulating material over the inductor coil 688 in a manner similar to that shown FIG. 90), while suitable materials for the inductor coil 688 include, but are not limited to copper, copper alloys, silver and other suitable metals.

It should also be noted that although the exemplary charging appliances in the embodiments illustrated in FIGS. 88-94 include inductors that extend around the wearer's neck, inductors that are configured to extend around other body structures may also be employed. Such charging appliances may, for example, include inductor apparatus that look like bracelets, belts, upper arm spirals, and other devices that extend (along with the inductor) around the perimeter of a bodily structure.

There is a wide variety of other charging appliances which include a wearable device that serves a purpose other than positioning an inductor (or charger) on the wearer's body. One such wearable device is an eyeglass frame and, to that end, the exemplary charging appliance 696 illustrated in FIG. 95 includes sunglasses 698 in addition to the inductor 24*a*, inductor related circuitry 25 and remote housing 104 (with the power supply and control apparatus and user interface). The sunglasses 698 consist of a frame 700, with a frame front 702 and a pair of arms 704, and lenses 706. A connector 536 is mounted on one of the arms 704 and the remote housing 104 may be connected to the inductor 24*a* and inductor related circuitry 25 by the connector 534 on cable 106*a*.

In the illustrated embodiment, the inductor 24*a* is carried within the frame front 702 and the charging of an implanted medical device, such as an implanted occipital nerve stimulator, would typically occur when the sunglasses 698 are being worn backwards. Alternatively, or in addition, an inductor may be carried within one or both of the arms 704. The frame 700 may be formed from materials such as plastics, ceramics and non-conducting metals to insulate the wearer from the inductor 24*a* and inductor related circuitry 25.

Figures 96, 97:
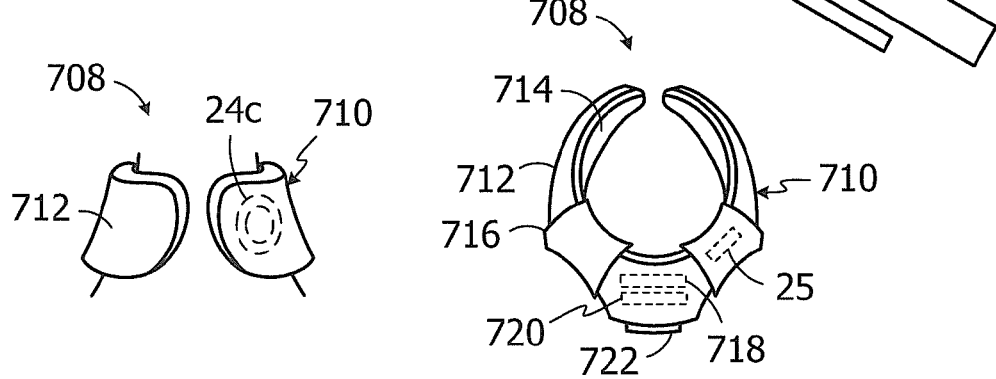
FIG. 96 is a front view of a charging appliance in accordance with one embodiment of a present invention.
FIG. 97 is a plan view of a portion of the charging appliance illustrated in FIG. 96.

Another example of a charging appliance which includes a wearable device that serves a purpose other than positioning an inductor (or charger) on the wearer's body is the charging appliance generally represented by reference numeral 708 in FIGS. 96 and 97. Here, an inductor 24*c* is incorporated into a personal cooler 710 that is worn on the neck and is suitably insulated from the wearer by, for example, a relatively soft plastic such as polyurethane. Although such charging appliances are not limited to any particular type of personal cooler, one example of such a personal cooler is the Personal Cooling System 3.0 sold by The Sharper Image. The personal cooler 710 includes a housing 712, an aluminum inner cooling surface 714, pads 716, a power supply 718, a controller 720, and a user interface 722. The personal cooler 710 also includes a fan and a water tank, which are not shown.

The power supply and control functionality associated with the inductor 24*c* in the exemplary charging appliance 708 may be performed by the personal cooler power supply 718 and controller 720 (as shown). Alternatively, a separate power supply and controller arrangement may be provided. The inductor related circuitry 25 may be positioned adjacent to the inductor 24*c* within the housing 712 (as shown), or may be eliminated and the functionality thereof added to the controller 720.

Figure 98:
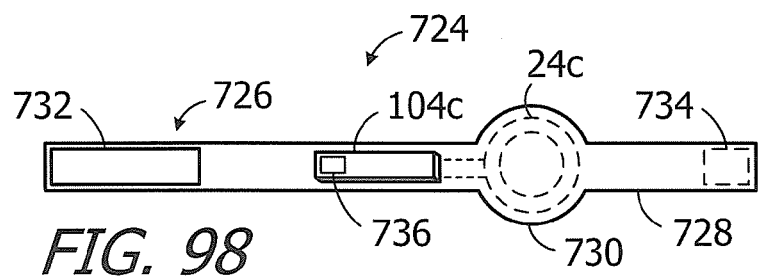
FIG. 98 is a plan view of a charging appliance in accordance with one embodiment of a present invention.

Turning to FIG. 98, the exemplary charging appliance 724 is configured such that all of its components may be mounted on the same portion of the wearer's body. More specifically, the charging appliance 724 includes a harness 726, an inductor 24*c* embedded within the harness and insulated from the wearer by, for example, a relatively soft plastic such as polyurethane, and a housing 104*c* mounted on the exterior of the harness. The exemplary harness 726 consists of a relatively narrow strap 728 with an enlarged portion 730 that carries the inductor 24*c*. The ends of the strap 728 may be secured to one another with any suitable fastener arrangement and, in the illustrated embodiment, hook and loop fastener strips 732 and 734 are employed. Suitable material for the harness 726 includes, but is not limited to, elastomeric material such as that sold under the trade name Neoprene. The elastomeric material may be covered with fabric to increase wearer comfort. The housing 104*c* carries the power supply and control apparatus and inductor related circuitry as well as the user interface (e.g. a button 736).

The exemplary charging appliance 724 is sized and shaped so as to be positioned on the wearer's neck. Such positioning is suitable for charging an implanted occipital nerve stimulator. Other implementations may be sized and shaped for positioning around one of the wearer's arms or legs, or the waist or the chest.

Figure 99:
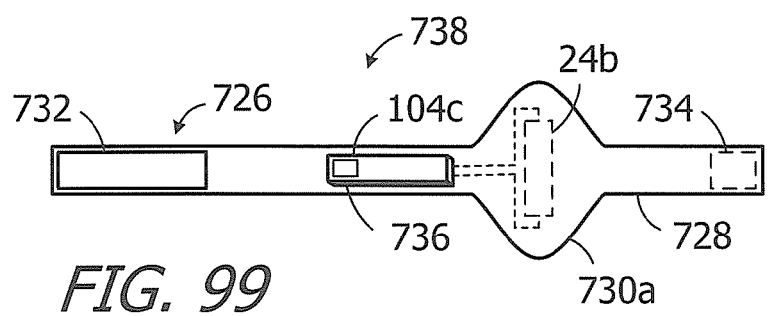
FIG. 99 is a plan view of a charging appliance in accordance with one embodiment of a present invention.

The exemplary charging appliance 738 illustrated in FIG. 99 is essentially identical to that illustrated in FIG. 98 and similar elements are represented by similar reference numerals. Here, however, the charging appliance includes coil 24*b* and the enlarged portion 730*a* of the strap is configured therefore. Like charging appliance 724, charging appliance 738 may be sized and shaped for placement around the neck, arm, leg, waist or chest.

Figure 100:
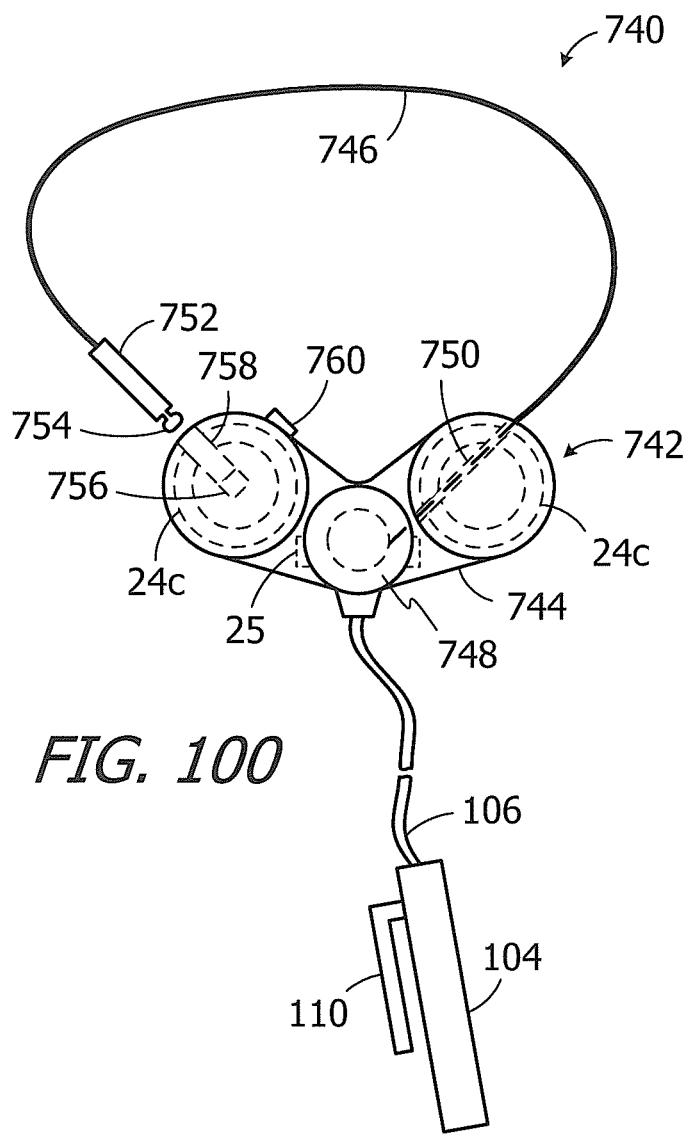
FIG. 100 is a plan view of a charging appliance in accordance with one embodiment of a present invention.

Turning to FIG. 100, exemplary charging appliance 740 is configured to position one or more inductors behind the wearer's neck. To that end, the exemplary charging appliance 740 includes an inductor apparatus 742 that is configured to be secured to the wearer's hair and a remote housing 104 with the above-described power supply and control apparatus and user interface.

The exemplary inductor apparatus 742 carries a pair of inductors 24*c* and inductor related circuitry 25. The inductors 24*c* and inductor related circuitry 25 may be molded into an epoxy, silicone, or urethane structure that is carried within a plastic housing 744. Alternatively, the inductors 24*c* and inductor related circuitry 25 may be carried within a polycarbonate housing, that is itself coated with an insulating encapsulate such as silicone, rubber-like polymers, Teflon, and other plastics. In either embodiment, the inductor apparatus 742 will be electrically insulated from the wearer and water resistant. The inductor apparatus 742 also includes a band 746 which performs the function of securing the housing 744 to the wearer's hair. The housing 744 may be provided in a variety of colors in order to allow the housing color to be matched to the wearer's hair color.

The housing 744 and band 746 may be secured to one another in a variety of ways. For example, each end of the band may be releasably secured to the housing by an appropriate fastener. In the illustrated embodiment, one end of the band 746 is secured to a spring biased reel 748 that is carried within the housing 744 and applies a tension force to the band. A lumen 750, which extends from the exterior of the housing to the reel 748, allows portions of the band 746 to move in and out of the housing 744. A dull needle 752, which facilitates threading of the band through the wearer's hair, may be secured to the other end of the band 746. The dull needle 752 also includes a latch element 754 that is configured to mate with a latch 756 within the housing. A lumen 758 allows the dull needle 752 to be inserted into the housing 744 and the latch 756 secures the dull needle to the housing 744 when the dull needle reaches the latch. A latch release button 760, which disconnects the latch element 754 from the latch 756 when pressed to allow the dull needle 752 to be pulled out of the lumen 758, is also provided.

With respect to the configuration of the band 746, the band may be formed from any suitable flexible material or combination thereof. The band 746 may be circular in cross-section (as shown), flat, or any other cross-sectional shape. In addition, the band 746 may be configured, e.g. through the use of a high friction material such as silicone rubber or a textured outer surface, to prevent slippage relative to the wearer's hair. The band 746 may also be provided in a variety of colors in order to allow the band color to be matched to the wearer's hair color.

In other implementations, the spring biased reel 748 may be replaced with a reel that has a handle which may be turned to reduce the exposed length of the band 746, a ratchet which maintains the band at the desired exposed length, and a ratchet release button which allows the exposed length of the band to be increased. The reel may also be omitted. Here, the length of the band 746 will be fixed. Regardless of the type of reel, or lack thereof, the other end of the band 746 may be releasably secured to the housing through the used of a twist lock arrangement instead of the above-described latch element 754, latch 756 and release button 760. The end of the band 746 opposite the reel may also be permanently secured to the housing. Here, the dull needle 752 may be omitted and, instead of threading the band 746 through the hair, the band 746 will simply be worn like a conventional hair band or sweat band.

The housing 104, as well as the power supply and control apparatus carried therein, are permanently connected to the inductor apparatus 742 by the cable 106 in the illustrated implementation. In other implementations, the cable may be permanently secured to one of the housing 104 and inductor apparatus 742 and releasable connected to the other by an appropriate connector arrangement, or releasable secured to both through the use of a cable with connectors at both ends.

It should also be noted here that inductors and inductor apparatus may be carried by and/or incorporated into a wide variety of wearable devices in addition those described above with reference to FIGS. 3-100. By way of example, but not limitation, such wearable devices include priest collars, fetal monitors, scuba suits, suspenders, body piercings, body tissue screws, head bands, splints, and gel pads.

III. Charging Appliances that may be Associated with Non-Wearable Devices

Charging appliances may also be carried by, part of, secured to and/or otherwise associated with non-wearable devices. In many instances, such non-wearable devices will be common, "everyday" devices that have utility which is entirely separate from the charging functionality.

Figure 101:
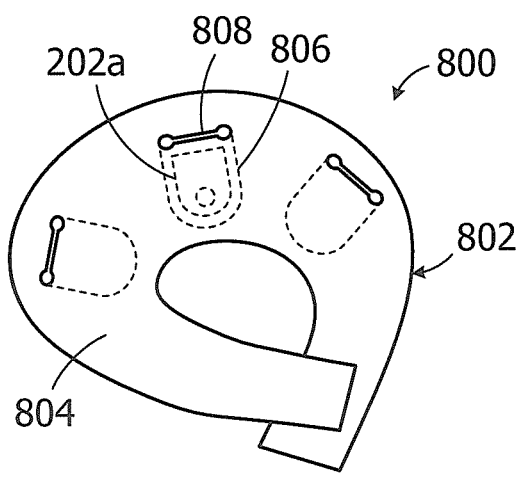
FIG. 101 is a plan view of a charging appliance in accordance with one embodiment of a present invention.

One such charging appliance is generally represented by reference numeral 800 in FIG. 101. The exemplary charging appliance 800 includes the above-described charger 202a and a pillow 802 (e.g. a cervical crescent pillow) that is configured to mount the charger in a plurality of different locations relative to the user. To that end, the exemplary pillow 802 includes a relatively soft, resilient body 804, formed from foam or other suitable material, and a plurality of pockets 806 with exterior openings 808 that are configured to receive the charger 202a. The pockets 806 can extend in one direction from the openings 808 (as shown), or in two directions. Additionally, although the illustrated embodiment includes three pockets, the number of pockets may be increased or decreased as desired.

Figure 102:
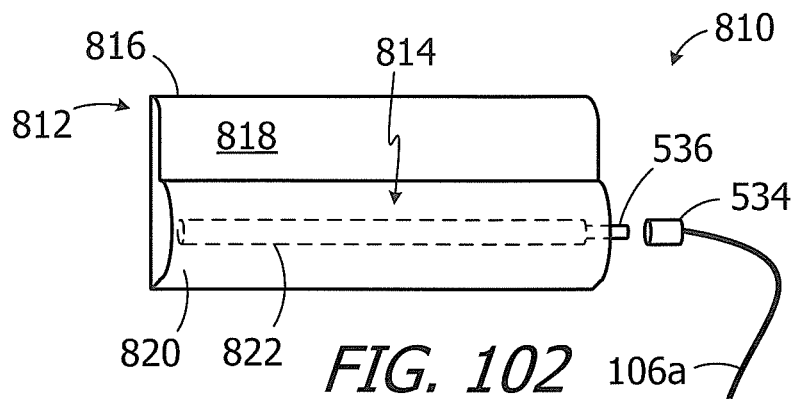
FIG. 102 is a perspective view of a charging appliance in accordance with one embodiment of a present invention.

Turning to FIG. 102, the exemplary charging appliance 810 illustrated therein includes a pillow 812, an inductor apparatus 814, and a remote housing 104d that is connected to the inductor apparatus. Although it is not limited to any particular type of pillow, the exemplary pillow 812 is a cervical comfort pillow with a relatively soft, resilient body 816, formed from foam or other suitable material, that has a relatively flat portion 818 and an enlarged portion 820. The inductor apparatus 814, which includes an inductor and inductor related circuitry (e.g. inductor 24a and inductor related circuitry 25), is positioned within the enlarged portion 820. Alternatively, or in addition, an inductor apparatus 814 may be positioned within the flat portion 818. The inductor and inductor related circuitry may be molded into an epoxy, silicone, or urethane structure that is carried within a plastic case 822. Alternatively, the inductor and inductor related circuitry may be carried within a polycarbonate case, that is itself coated with an insulating encapsulate such as silicone, rubber-like polymers, Teflon, and other plastics.

In addition to the power supply and control apparatus, the remote housing 104d includes a user interface 105, which consists of a display and a plurality of buttons. A cable 106a may be used to connect the power supply and control apparatus within the remote housing 104d to, or disconnect the power supply and control apparatus from, the inductor apparatus 814. To that end, one end of the cable 106a is connected to the remote housing 104d and the other has a connector 534 that is configured to mate with a corresponding connector 536 that is associated with the inductor apparatus 814. In other implementations, the cable 106a may be permanently secured to the inductor apparatus 814 and the connector 534 used to connect the cable to the remote housing, the cable may be permanently secured to both, or a cable with connectors at both ends may be provided.

It should also be noted here that an otherwise conventional pillow may be converted into a charging appliance by combining the pillow with a pillow case that includes one or more pockets for a charger. Another alternative is to connect the charging appliance 200 illustrated in FIGS. 3-6 to a pillow case.

Figure 103:
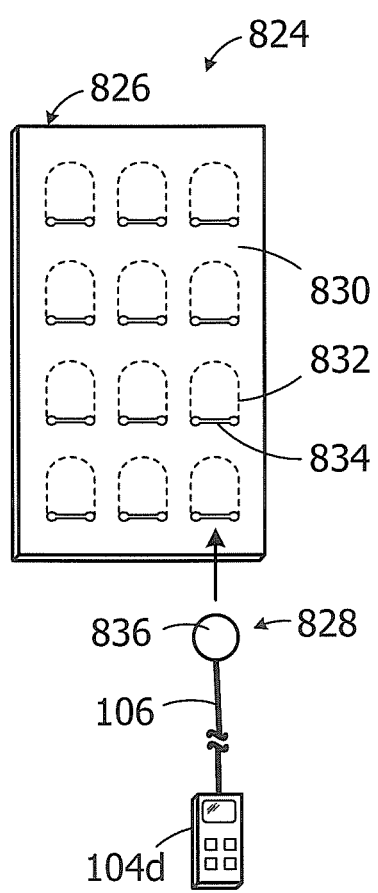
FIG. 103 is a perspective view of a charging appliance in accordance with one embodiment of a present invention.

Another charging appliance that includes a non-wearable device is generally represented by reference numeral 824 in FIG. 103. The exemplary charging appliance includes a mattress pad 826, an inductor apparatus 828, and the remote housing 104d. The mattress pad 826 includes a relatively soft, resilient body 830, formed from foam, goose down covered by an outer fabric, or any other suitable material. The mattress pad 826 is also configured to mount the inductor apparatus 828 in a plurality of different locations relative to the user and, to that end, has a plurality of pockets 832 with exterior openings 834 that are configured to receive the inductor apparatus. The choice of pocket 832 will depend on the location of the implanted medical device. In the illustrated embodiment, the pockets 832 extend downwardly into the resilient body 830 so that some of the resilient body will between the wearer and the inductor apparatus 828 to insure that the inductor apparatus does not render the mattress pad uncomfortable. The pockets 832 can also extend in one direction from the openings 834 (as shown), or in two directions. Additionally, the number of pockets may be increased or decreased as desired.

The inductor apparatus 828 includes an inductor and inductor related circuitry (e.g. inductor 24c and inductor related circuitry 25) which are molded into an epoxy, silicone, or urethane structure that is carried within a plastic case 836. Alternatively, the inductor and inductor related circuitry may be carried within a polycarbonate case, that is itself coated with an insulating encapsulate such as silicone, rubber-like polymers, Teflon, and other plastics. A cable 106 connects the inductor and inductor related circuitry carried by the inductor apparatus 828 to the power supply and control apparatus carried by the remote housing 104d.

Figure 104:
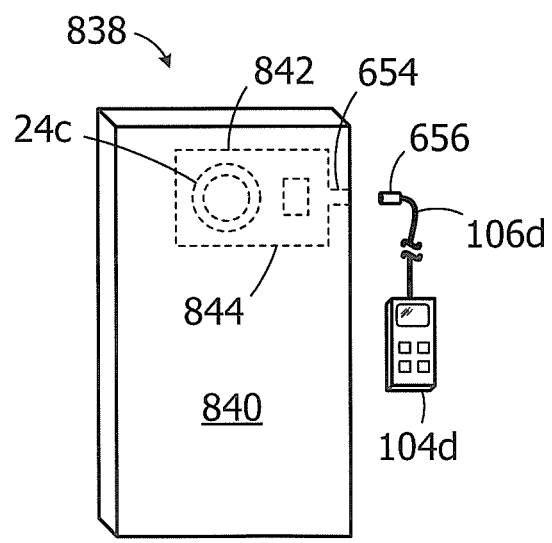
FIG. 104 is a perspective view of a charging appliance in accordance with one embodiment of a present invention.

Other charging appliances include the mattress itself. One such charging appliance, which is generally represented by reference numeral 838 in FIG. 104, includes a mattress 840, an inductor apparatus 842 mounted within the mattress, and the remote housing 104d. The exemplary inductor apparatus 842 includes an inductor and inductor related circuitry (e.g. inductor 24c and inductor related circuitry 25) which are molded into an epoxy, silicone, or urethane structure that is carried within a plastic case 844. Alternatively, the inductor and inductor related circuitry may be carried within a polycarbonate case, that is itself coated with an insulating encapsulate such as silicone, rubber-like polymers, Teflon, and other plastics. The power supply and control apparatus within the remote housing 104d is connected to the inductor apparatus 842 by way of the inductor apparatus connector 654, which is positioned at the side edge of the mattress 840, and the connector 656 on the cable 106d. In other implementations, the cable may be permanently secured to the inductor apparatus and a connector used to connect the cable to the remote housing, or a cable with connectors at both ends may be provided.

Figure 105:
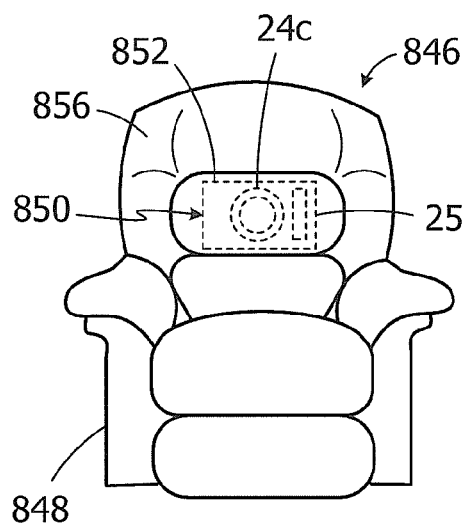
FIG. 105 is a front view of a charging appliance in accordance with one embodiment of a present invention.
Figure 106:
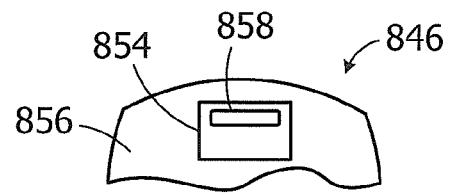
FIG. 106 is a rear view of a portion of the charging appliance illustrated in FIG. 105.

Chairs, couches, and like are other examples of non-wearable devices that may form part of a charging appliance and, to that end, the exemplary charging appliance 846 illustrated in FIGS. 105 and 106 includes a recliner chair 848. An inductor apparatus 850, which is mounted within the recliner chair 848, includes an inductor and inductor related circuitry (e.g. inductor 24c and inductor related circuitry 25) which are molded into an epoxy, silicone, or urethane structure that is carried within a flexible plastic case 852. Alternatively, the inductor and inductor related circuitry may be carried within a flexible polycarbonate case, that is itself coated with an insulating encapsulate such as silicone, rubber-like polymers, Teflon, and other plastics. A housing 854 is mounted, in the illustrated embodiment, on the top rear portion of the backrest 856. The housing 854 includes the power supply and control apparatus and is directly connected to the inductor apparatus 850. The exemplary housing 854 also includes a user interface in the form of a relatively large button 858.

It should be noted here that the location of the inductor apparatus 850 and housing 854 may be varied as desired. The housing 854 may also be removed from the chair and connected to the inductor and inductor related circuitry by way of a cable.

Figure 107:
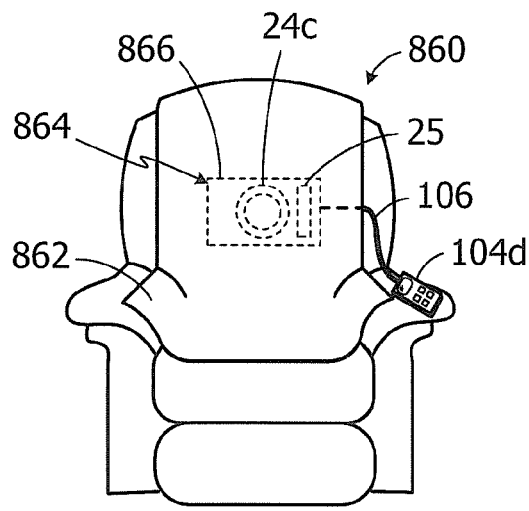
FIG. 107 is a front view of a charging appliance in accordance with one embodiment of a present invention.

Turning to FIG. 107, the exemplary charging appliance 860 illustrated therein includes a seat cover 862, an inductor apparatus 864 carried by the seat cover, and a housing 104d connected to the inductor apparatus by a cable 106. The exemplary inductor apparatus 864 includes an inductor and inductor related circuitry (e.g. inductor 24c and inductor related circuitry 25) which are molded into an epoxy, silicone, or urethane structure that is carried within a flexible plastic case 866. Alternatively, the inductor and inductor related circuitry may be carried within a flexible polycarbonate case, that is itself coated with an insulating encapsulate such as silicone, rubber-like polymers, Teflon, and other plastics. The charging appliance 860 may be positioned on the underlying piece of furniture as required to bring the inductor into close proximity with the user's implanted medical device.

Other exemplary charging appliances include a charger, such as the above-described charger 202a, in combination with a chair, couch, seat cover or the like which has one or more pockets that are configured to receive the charger.

Figure 108:
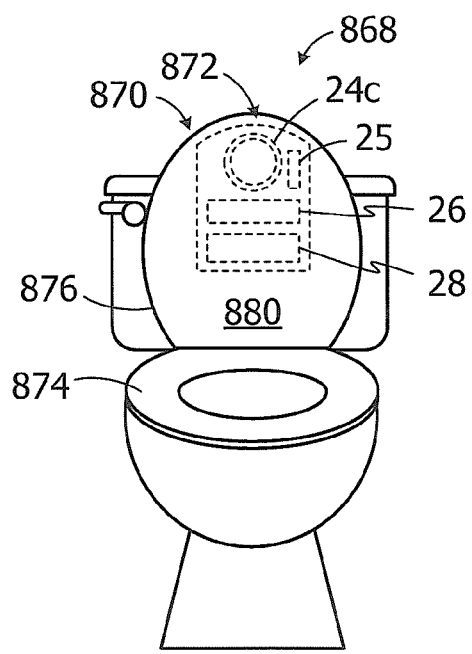
FIG. 108 is a front view of a charging appliance in accordance with one embodiment of a present invention.
Figure 109:
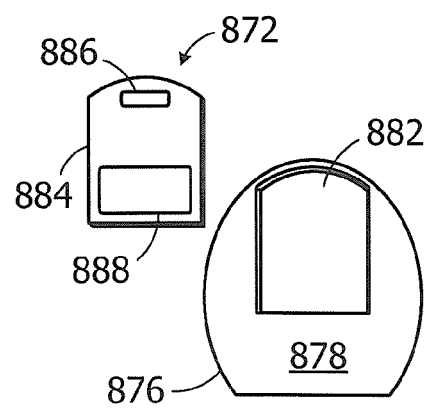

The exemplary charging appliance 868 illustrated in FIGS. 108 and 109 includes a toilet seat assembly 870 and a charger 872 that may be mounted in the toilet seat assembly. The exemplary toilet seat assembly 870 includes include a seat 874 and cover 876 with a top side 878 and a bottom side 880. The top side 878 has an indentation 882. The charger 872 includes an inductor 24c, inductor related circuitry 25, a power supply 26, and a controller 28 that are carried with a housing 884. The housing 884 is sized and shaped to fit within the indentation 882, and the exterior of the housing includes a user interface (e.g. button 886) and a door 888 to facilitate replacement of the power supply 26.

Figure 110:
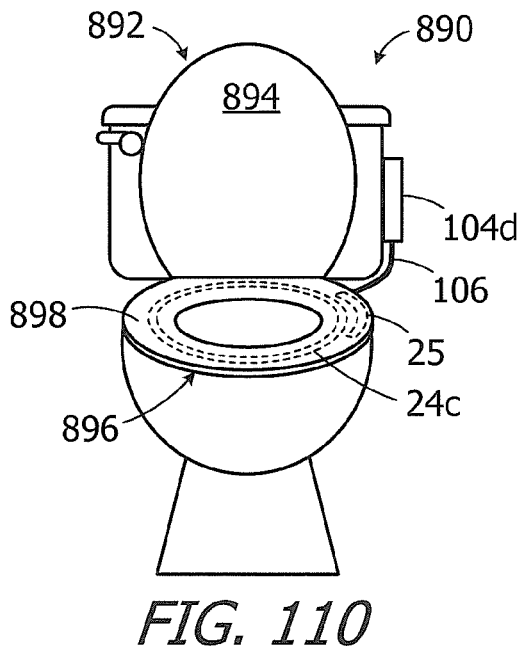

Another exemplary toilet related charging appliance, which is generally represented by reference numeral 890 in FIG. 110, includes a toilet seat assembly 892, with a seat cover 894 and an inductor apparatus 896 that also functions as a toilet seat, and a housing 104d that includes the power supply and control apparatus. The exemplary inductor apparatus 896 includes an inductor and inductor related circuitry (e.g. inductor 24c and inductor related circuitry 25) which are molded into an insulting plastic (e.g. PVC) structure 898, or added to a wood or porcelain structure, that is shaped like a toilet seat.

In the illustrated embodiment, the housing 104d is mounted on the toilet tank and is connected to the inductor apparatus 896 by a cable 106. Alternatively, one or both of the housing 104d and inductor apparatus 896 may be provided with a connector, and one or both of the ends of the associated cable may be provided with a corresponding connector, in order to allow the housing to be selectively connected to and disconnected from the inductor apparatus 896. In other implementations, the housing and components associated therewith may be incorporated into the toilet seat.

Figure 111:
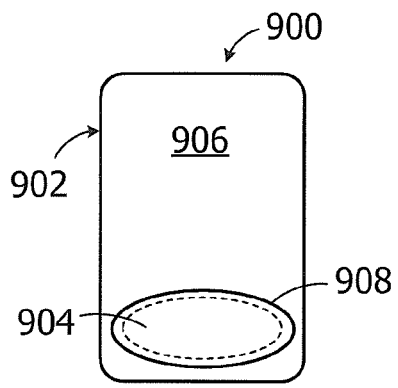
Figure 112:
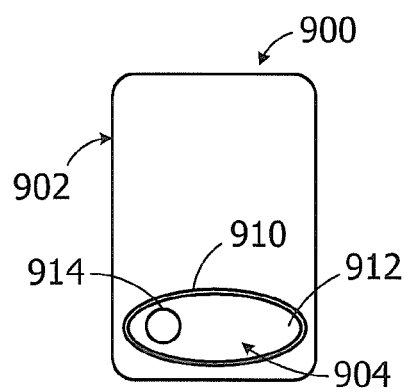

Turning to FIGS. 111 and 112, the exemplary charging appliance 900 consists of a mouse pad 902 and a charger 904. The exemplary mouse pad 902 includes a flat mouse portion 906 and a wrist rest 908 that is configured to receive the charger 904. To that end, the bottom surface of the mouse pad 902 includes an aperture 910 for the charger 904 that is aligned with the wrist rest 908. In addition to the above-described power supply, controller, inductor and inductor related circuitry, the charger 904 includes a housing with a flat bottom surface 912, which is aligned with the bottom surface of the mouse pad, and a user interface (e.g. button 914) on the bottom surface.

Figure 113:
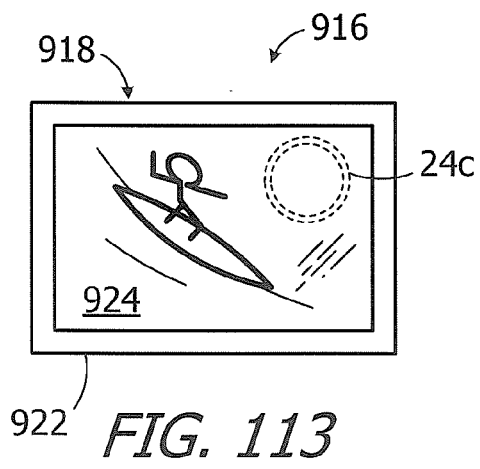
Figure 114:
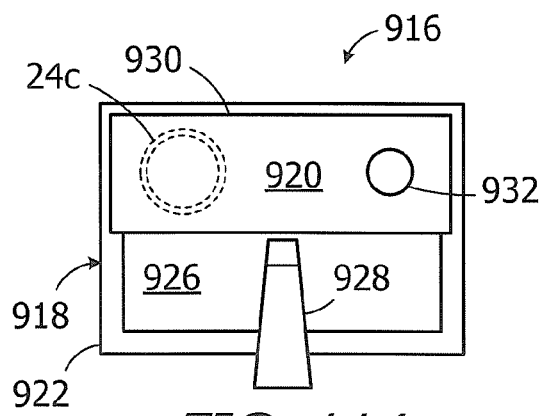

A picture frame is another example of a non-wearable device that may form part of a charging appliance. More specifically, the charging appliance generally represented by reference numeral 916 in FIGS. 113 and 114 includes a picture frame 918 and a charger 920 carried on the back of the frame. The exemplary picture frame 918 is a desktop frame that includes a border 922, a glass (or clear plastic) front panel 924, a backing 926, a support arm 928. In addition to the above-described power supply, controller, inductor (e.g. inductor 24c) and inductor related circuitry, the charger 920 includes a housing 930 that is secured to the rear surface of the border 922. A user interface (e.g. button 932) is positioned on the exterior of the housing 930.

The charging appliance 916 may be placed on a desk, nightstand, table or other suitable location that will result in the inductor being in close proximity an implanted medical device. It should also be noted that wall mounted frames, which are intended for placement in close proximity to the user (e.g. within a cubical or other small workstation), may be employed in combination with a suitable charger.

Non-wearable devices that may form part of a charging appliance also include devices associated with automobiles. Referring first to FIG. 115, the exemplary charging appliance 934 includes a seat cover 936, an inductor apparatus 938 that is secured to the inner surface of the seat cover, and a housing 104d that is associated with the outer surface of the seat cover. The seat cover 936, which may be formed from fabric, sheepskin, or any other suitable material, is sized and shaped to fit over the underlying automobile seat 940. The exemplary inductor apparatus 938 includes an inductor and inductor related circuitry (e.g. inductor 24a and inductor related circuitry 25) which are molded into an epoxy, silicone, or urethane structure that is carried within a flexible plastic case. The housing 104d is connected to the inductor apparatus 938 by a cable (not shown).

The illustrated position of the inductor apparatus 938, i.e. adjacent to the headrest 942, is suitable for charging an implanted occipital nerve stimulator. In other implementations, the inductor apparatus 938 may be secured to the seat cover 936 at locations corresponding to the automobile seat backrest 944 or thigh support 946.

A charging appliance may, alternatively, include a portion of the automobile seat itself. As illustrated for example in FIG. 116, the exemplary charging appliance 948 includes an automobile seat 950, an inductor apparatus 952 that is mounted within the seat, and a housing 954 that is also mounted with the seat. The exemplary inductor apparatus 952 includes an inductor and inductor related circuitry (e.g. inductor 24a and inductor related circuitry 25) which are molded into an epoxy, silicone, or urethane structure that is carried within a flexible plastic case. The housing 954, which carries the above-described power supply and control apparatus and is connected to the inductor apparatus 952 by a cable (not shown), is mounted with the seat 950 such that a portion of the housing is accessible. The accessible portion of the housing 954 includes a user interface (e.g. button 956) and a door 958 to facilitate replacement of the power supply.

The position of the inductor apparatus 952 in the illustrated embodiment, i.e. within the headrest 960, is suitable for charging an implanted occipital nerve stimulator. In other implementations, the inductor apparatus and, in some instances the housing, may be positioned within the automobile seat backrest or thigh support. Still other charging appliances may include inductor apparatus in a plurality of locations within the seat (e.g. within the headrest, the backrest and the thigh support).

Turning to FIG. 117, the exemplary charging appliance 962 includes an automobile steering wheel 964 and an inductor 966 that is embedded within the steering wheel. More specifically, exemplary inductor 966 is molded into a steering wheel formed from an insulating plastic (e.g. PVC). A housing 968 is positioned within an indentation in steering wheel 964, and the above-described power supply, controller and inductor related circuitry are located within the housing. The exterior portion of the housing 968 that faces away from the steering wheel 964 includes a user interface (e.g. button 970) and a door 972 that facilitates replacement of the power supply.

By way of example, but not limitation, other automotive-related device that may form part of a charging appliance include steering wheel covers, window visors, floor mats, and seat belts.

Although the inventions disclosed herein have been described in terms of the preferred embodiments above, numerous modifications and/or additions to the above-described preferred embodiments would be readily apparent to one skilled in the art. By way of example, but not limitation, a grounded electric shield, which will not interfere with charging, may be added to any of embodiments described above and positioned such that it will be located between the inductive coil and the wearer. It is intended that the scope of the present inventions extend to all such modifications and/or additions and that the scope of the present inventions is limited solely by the claims set forth below.

We claim:

1. A charging appliance, comprising:
    a charger for charging a medical device implanted in a patient; and
    a mounting apparatus comprising a shoulder drape and a counterweight for the charger, the shoulder drape having a first free end carrying at least one pocket configured to receive the charger and a second free end carrying the counterweight.

2. The charging appliance of claim 1, wherein the counterweight comprises an additional charger.

3. The charging appliance of claim 1, wherein the counterweight is removable from the mounting apparatus.

4. The charging appliance of claim 1, wherein the shoulder drape has a fixed curved shape.

5. The charging appliance of claim 1, wherein the shoulder drape includes a slip resistant surface.

6. The treatment system of claim 1, wherein the first and second free ends are configured to be positioned at opposing sides of the patient's body.

7. The treatment system of claim 1, wherein the shoulder drape extends along a longitudinal axis, and is bi-symmetrical about a line that is transverse to the longitudinal axis.

8. A treatment system to be used with a patient, comprising:
    an implantable pulse generator (IPG) that is implantable in the patient's body;
    a charger to charge the IPG, wherein the charger is positionable outside the patient's body; and
    a mounting apparatus comprising a shoulder drape and a counterweight for the charger, the shoulder drape having a first free end carrying at least one pocket configured to receive the charger and a second free end carrying the counterweight.

9. The treatment system of claim 8, further comprising a lead coupled to the IPG and configured to extend into a selected portion of the patient's body.

10. The treatment system of claim 9, wherein the lead is configured to be implanted in the patient's brain for deep brain stimulation.

11. The treatment system of claim 9, wherein the lead is configured to be implanted in the patient's neck for headache treatment.

12. The treatment system of claim 8, wherein the charger is powered by a rechargeable battery contained in the charger.

13. The treatment system of claim 8, wherein the counterweight comprises an additional charger.

14. The treatment system of claim 8, wherein the counterweight is removable from the mounting apparatus.

15. The treatment system of claim 8, wherein the shoulder drape has a fixed curved shape.

16. The treatment system of claim 8, wherein the shoulder drape includes a slip resistant surface.

17. The treatment system of claim 8, wherein the first and second free ends are configured to be positioned at opposing sides of the patient's body.

18. The treatment system of claim 8, wherein the shoulder drape extends along a longitudinal axis, and is bi-symmetrical about a line that is transverse to the longitudinal axis.

* * * * *